(12) United States Patent
Quaranta et al.

(10) Patent No.: US 11,124,508 B2
(45) Date of Patent: Sep. 21, 2021

(54) FUNGICIDAL COMPOSITIONS

(71) Applicant: SYNGENTA PARTICIPATIONS AG, Basel (CH)

(72) Inventors: Laura Quaranta, Stein (CH); Stephan Trah, Stein (CH); Matthias Weiss, Stein (CH); Farhan Bou Hamdan, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/486,525

(22) PCT Filed: Feb. 14, 2018

(86) PCT No.: PCT/EP2018/053624
§ 371 (c)(1),
(2) Date: Aug. 16, 2019

(87) PCT Pub. No.: WO2018/149851
PCT Pub. Date: Aug. 23, 2018

(65) Prior Publication Data
US 2020/0002333 A1 Jan. 2, 2020

(30) Foreign Application Priority Data
Feb. 16, 2017 (EP) .................................. 17156509

(51) Int. Cl.
*C07D 471/04* (2006.01)
*A01N 43/90* (2006.01)

(52) U.S. Cl.
CPC ........... *C07D 471/04* (2013.01); *A01N 43/90* (2013.01)

(58) Field of Classification Search
CPC .............................. C07D 471/04; A01N 43/90
See application file for complete search history.

(56) References Cited

FOREIGN PATENT DOCUMENTS

| EP | 2517562 A1 | 10/2012 |
| WO | 2016156085 A1 | 10/2016 |
| WO | 2017025509 A1 | 2/2017 |

OTHER PUBLICATIONS

ISR & Written Opinion for PCT/EP2018/053624, dated Apr. 16, 2018.

*Primary Examiner* — Yong S. Chong
(74) *Attorney, Agent, or Firm* — BakerHostetler; Toni-Junell Herbert

(57) ABSTRACT

A fungicidal composition comprising a mixture of components (A) and (B), wherein components (A) and (B) are as defined in claim 1, and use of the compositions in agriculture or horticulture for controlling or preventing infestation of plants by phytopathogenic microorganisms, preferably fungi.

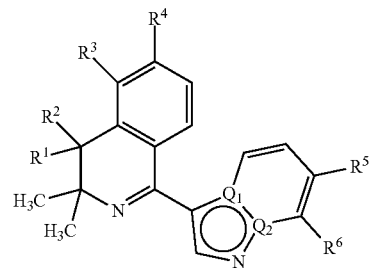

(I)

20 Claims, No Drawings

FUNGICIDAL COMPOSITIONS

CROSS-REFERENCE TO RELATED APPLICATIONS

This application is a 371 National Stage application of International Application No. PCT/EP2018/053624, filed Feb. 14, 2018, which claims priority to EP 17156509.6 filed Feb. 16, 2017, the entire contents of which applications are hereby incorporated by reference.

The present invention relates to novel fungicidal compositions, to their use in agriculture or horticulture for controlling diseases caused by phytopathogens, especially phytopathogenic fungi, and to methods of controlling diseases on useful plants, especially fruits and vegetables.

Certain heterobicyclic compounds have been proposed in the literature as microbiocidal active ingredients in pesticides. For example, WO 05/070917 discloses heterobicyclic compounds which are described to be useful as fungicides. Further, whilst many fungicidal compounds and compositions, belonging to various different chemical classes, have been/are being developed for use as fungicides in crops of useful plants, crop tolerance and activity against particular phytopathogenic fungi do not always satisfy the needs of agricultural practice in many respects.

There is therefore a continuing need to find new compounds and new compositions having superior biological properties for use in controlling or preventing infestation of plants by phytopathogenic fungi; for example, compounds possessing a greater biological activity, an advantageous spectrum of activity, an increased safety profile, improved physico-chemical properties, increased biodegradability, or compositions possessing a broader of spectrum of activity, improved crop tolerance, synergistic interactions or potentiating properties, or compositions which display a more rapid onset of action or which have longer lasting residual activity or which enable a reduction in the number of applications and/or a reduction in the application rate of the compounds and compositions required for effective control of a phytopathogen, thereby enabling beneficial resistance-management practices, reduced environmental impact and reduced operator exposure.

The use of compositions comprising mixtures of different fungicidal compounds possessing different modes of action can address some of these needs (e.g. by combining fungicides with differing spectrums of activity).

The present invention therefore provides novel fungicidal compositions comprising as active ingredients a mixture of component (A) and component (B), wherein component (A) is a compound of formula (I)

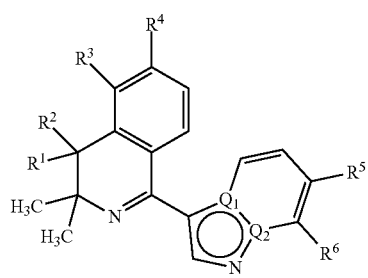

wherein
$Q_1$ is a nitrogen atom and $Q_2$ is a carbon atom; or
$Q_1$ is a carbon atom and $Q_2$ is a nitrogen atom; and
$R^1$ is fluoro or methyl;
$R^2$ is fluoro or methyl;
$R^3$ is hydrogen or fluoro;
$R^4$ is hydrogen, or fluoro;
$R^5$ is hydrogen, methyl, ethyl, fluoro, chloro or bromo;
$R^6$ is hydrogen or methyl; or a salt or N-oxide thereof; and
component (B) is a compound selected from the group consisting of:
Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In general, the weight ratio of component (A) to component (B) is from 20:1 to 1:40, especially from 15:1 to 1:30, more especially in a ratio from 12:1 to 1:25, even more especially in a ratio of from 10:1 to 1:20, very especially in a ratio from from 5:1 and 1:20, and still more especially in a ratio from 2:1 to 1:5.

The benefits provided by certain mixture compositions according to the invention may also include, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

The presence of one or more possible asymmetric carbon atoms in a compound of formula (I) means that the compounds may occur in optically isomeric forms, i.e. enantiomeric or diastereomeric forms. The specific substitution pattern at the carbon atom to which $R^2$ is attached means that the compounds of formula (I) occur in (at least) two enantiomeric forms. Also atropisomers may occur as a result of restricted rotation about a single bond. The present invention includes all those possible isomeric forms (e.g. geometric isomers) and mixtures thereof for a compound of formula (I). Likewise, formula (I) is intended to include all possible tautomers. The present invention includes all possible tautomeric forms for a compound of formula (I), and also a racemic compound, i.e. a mixture of at least two enantiomers in a ratio of substantially 50:50.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred groups and values for the substituents $R^2$, $R^3$, $R^4$, $R^5$ and $R^6$ in the compounds of formula (I) are, in any combination thereof, as set out below.

Preferably $R^1$ and $R^2$ are both fluoro;
Preferably $R^3$ and $R^4$ are both hydrogen;
Preferably $R^5$ is fluoro, chloro or methyl;
Preferably $R^6$ is hydrogen or methyl, in particular, methyl;
or a salt, enantiomer, tautomer or N-oxide of such compounds.

In one embodiment of the compounds of Formula (I) for component (A), $Q_1$ is a nitrogen atom and $Q_2$ is a carbon atom. In another embodiment of the compounds of Formula (I) for component (A), $Q_1$ is a carbon atom and $Q_2$ is a nitrogen atom.

Most preferably, component (A) is a compound selected from compound no. X.001, X.002, X.003, X.004, X.005, X.006, X.007, X.008, X.009, X.010, X.011, X.012, X.013, X.014, X.015, X.016, X.017, X.018, X.019, as defined in the Table X below:

TABLE X

| Compound number | Compound structure | IUPAC name |
| --- | --- | --- |
| X.001 | 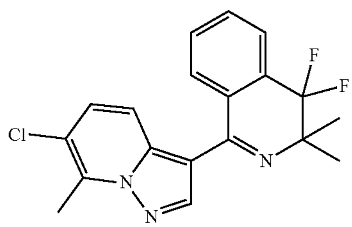 [SMILES: Cc1c(Cl)ccc2c(C3=NC(C)(C)C(F)(F)c4ccccc43)cnn12] | 1-(6-chloro-7-methyl-pyrazolo[1,5-a]pyridin-3-yl)-4,4-difluoro-3,3-dimethyl-isoquinoline |
| X.002 | 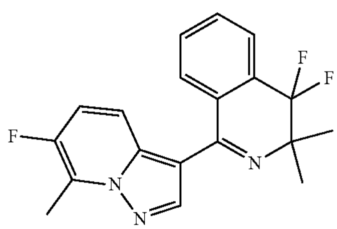 [SMILES: Cc1c(F)ccc2c(C3=NC(C)(C)C(F)(F)c4ccccc43)cnn12] | 4,4-difluoro-1-(6-fluoro-7-methyl-pyrazolo[1,5-a]pyridin-3-yl)-3,3-dimethyl-isoquinoline |
| X.003 | 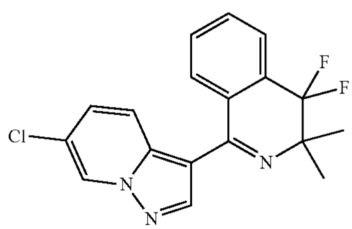 [SMILES: CC1(C)N=C(c2cnn3cc(Cl)ccc23)c2ccccc2C1(F)F] | 1-(6-chloropyrazolo[1,5-a]pyridin-3-yl)-4,4-difluoro-3,3-dimethyl-isoquinoline |
| X.004 | 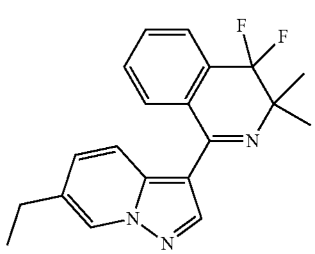 [SMILES: CCc1ccc2c(C3=NC(C)(C)C(F)(F)c4ccccc43)cnn2c1] | 1-(6-ethylpyrazolo[1,5-a]pyridin-3-yl)-4,4-difluoro-3,3-dimethyl-isoquinoline |
| X.005 | 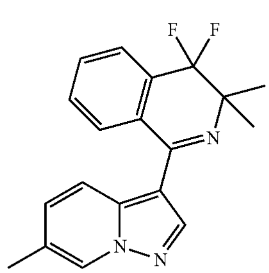 | 4,4-difluoro-3,3-dimethyl-1-(6-methylpyrazolo[1,5-a]pyridin-3-yl)isoquinoline |

TABLE X-continued

| Compound number | Compound structure | IUPAC name |
| --- | --- | --- |
| X.006 | 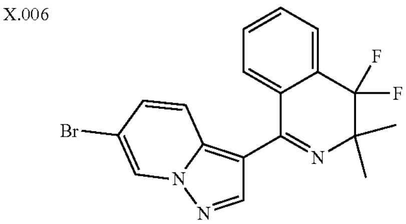 | 1-(6-bromopyrazolo[1,5-a]pyridin-3-yl)-4,4-difluoro-3,3-dimethyl-isoquinoline |
| X.007 | 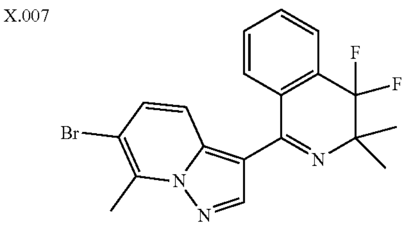 | 1-(6-bromo-7-methyl-pyrazolo[1,5-a]pyridin-3-yl)-4,4-difluoro-3,3-dimethyl-isoquinoline |
| X.008 | 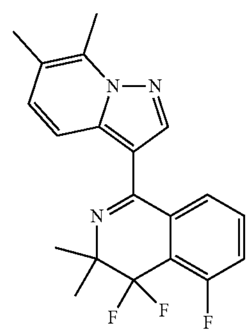 [SMILES: Cc1ccc2c(C3=NC(C)(C)C(F)(F)c4c(F)cccc43)cnn2c1C] | 1-(6,7-dimethylpyrazolo[1,5-a]pyridin-3-yl)-4,4,5-trifluoro-3,3-dimethyl-isoquinoline |
| X.009 | 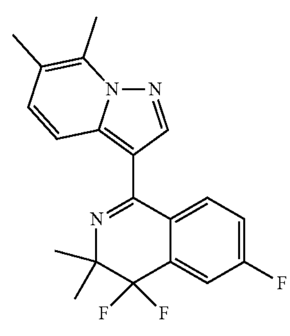 [SMILES: Cc1ccc2c(C3=NC(C)(C)C(F)(F)c4cc(F)ccc43)cnn2c1C] | 1-(6,7-dimethylpyrazolo[1,5-a]pyridin-3-yl)-4,4,6-trifluoro-3,3-dimethyl-isoquinoline |
| X.010 | 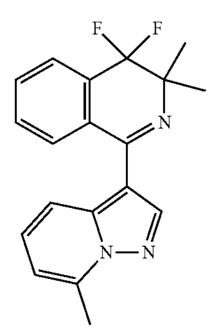 [SMILES: Cc1cccc2c(C3=NC(C)(C)C(F)(F)c4ccccc43)cnn12] | 4,4-difluoro-3,3-dimethyl-1-(7-methylpyrazolo[1,5-a]pyridin-3-yl)isoquinoline |

TABLE X-continued

| Compound number | Compound structure | IUPAC name |
|---|---|---|
| X.011 | 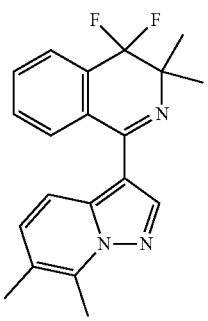 | 1-(6,7-dimethylpyrazolo[1,5-a]pyridin-3-yl)-4,4-difluoro-3,3-dimethyl-isoquinoline |
| X.012 | 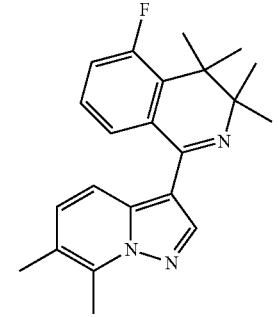 | 1-(6,7-dimethylpyrazolo[1,5-a]pyridin-3-yl)-5-fluoro-3,3,4,4-tetramethyl-isoquinoline |
| X.013 | 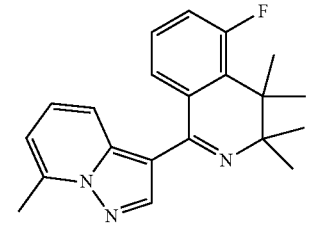 | 5-fluoro-3,3,4,4-tetramethyl-1-(7-methylpyrazolo[1,5-a]pyridin-3-yl)isoquinoline |
| X.014 | 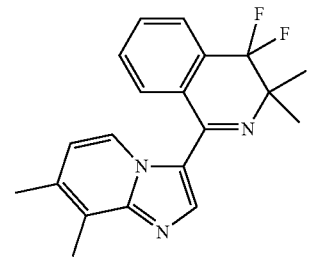 | 1-(7,8-dimethylimidazo[1,2-a]pyridin-3-yl)-4,4-difluoro-3,3-dimethyl-isoquinoline |
| X.015 | 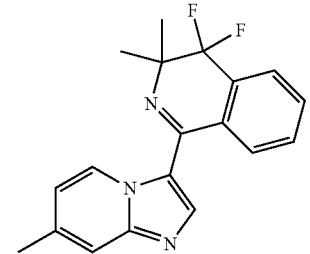 [SMILES: Cc1ccn2c(C3=NC(C)(C)C(F)(F)c4ccccc43)cnc2c1] | 4,4-difluoro-3,3-dimethyl-1-(7-methylimidazo[1,2-a]pyridin-3-yl)isoquinoline |
| X.016 | 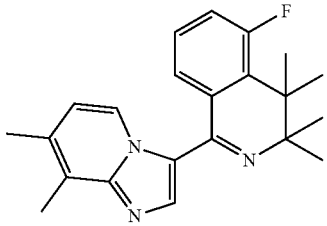 | 1-(7,8-dimethylimidazo[1,2-a]pyridin-3-yl)-5-fluoro-3,3,4,4-tetramethyl-isoquinoline |
| X.017 | 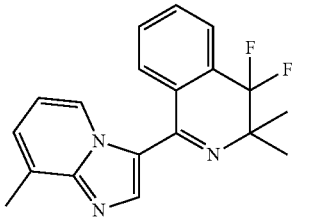 [SMILES: Cc1cccn2c(C3=NC(C)(C)C(F)(F)c4ccccc43)cnc12] | 4,4-difluoro-3,3-dimethyl-1-(8-methylimidazo[1,2-a]pyridin-3-yl)isoquinoline |
| X.018 | 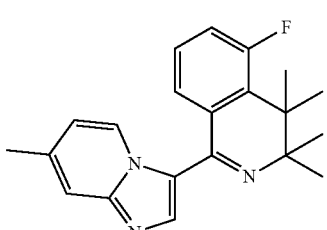 | 5-fluoro-3,3,4,4-tetramethyl-1-(7-methylimidazo[1,2-a]pyridin-3-yl)isoquinoline |
| X.019 | 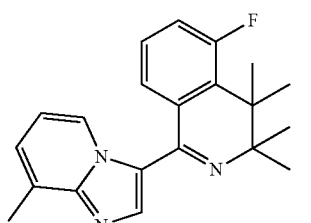 | 5-fluoro-3,3,4,4-tetramethyl-1-(8-methylimidazo[1,2-a]pyridin-3-yl)isoquinoline |

Preferably, component (B) is a compound selected from the group consisting of Pydiflumetofen, Benzovindiflupyr [1072957-71-1], Difenoconazole, Azoxystrobin, Fludioxonil, Fluazinam, Cyprodinil, Isopyrazam, Pyroquilon, Tricyclazole and Chlorothalonil. More preferably, component (B) is a compound selected from the group consisting of Pydiflumetofen, Difenoconazole, Azoxystrobin, Fludioxonil, Cyprodinil and Pyroquilon.

The component (B) compounds are referred to herein above by a so-called "ISO common name" or another "common name" being used in individual cases or a trademark name. The component (B) compounds are known and are commercially available and/or can be prepared using procedures known in the art and/or procedures reported in the literature.

In a preferred composition according to the invention component (A) is compound no. X.001 [146-chloro-7-methyl-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.002 [4,4-difluoro-1-(6-fluoro-7-methyl-pyrazolo[1,5-a]pyridin-3-yl)-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.003 [1-(6-chloro-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.004 [1-(6-ethylpyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.005 [4,4-difluoro-3,3-dimethyl-1-(6-methylpyrazolo[1,5-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.006 [1-(6-bromopyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.007 [1-(6-bromo-7-methyl-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.008 [1-(6,7-dimethylpyrazolo[1,5-a]pyridin-3-yl)-4,4,5-trifluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.009 [1-(6,7-dimethylpyrazolo[1,5-a]pyridin-3-yl)-4,4,6-trifluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.010 [4,4-difluoro-3,3-dimethyl-1-(7-methylpyrazolo[1,5-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.011 [1-(6,7-dimethylpyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.012 [1-(6,7-dimethylpyrazolo[1,5-a]pyridin-3-yl)-5-fluoro-3,3,4,4-tetramethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.013 [5-fluoro-3,3,4,4-tetramethyl-1-(7-methylpyrazolo[1,5-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.014 [1-(7,8-dimethylimidazo[1,2-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.015 [4,4-difluoro-3,3-dimethyl-1-(7-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.016 [1-(7,8-dimethylimidazo[1,2-a]pyridin-3-yl)-5-fluoro-3,3,4,4-tetramethyl-isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.017 [4,4-difluoro-3,3-dimethyl-1-(8-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.018 [5-fluoro-3,3,4,4-tetramethyl-1-(7-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In another preferred composition according to the invention component (A) is compound no. X.019 [5-fluoro-3,3,4,4-tetramethyl-1-(8-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Hexaconazole, Azoxystrobin, Fludioxonil, Cyprodinil, Fluazinam, Isopyrazam, Pyroquilon, Tricyclazole, Chlorothalonil, Propiconazole, Penconazole, Fenpropimorph, Fenpropidin, Sulfur, and *Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) to component (B) is from 20:1 to 1:40.

In a more preferred composition according to the invention component (A) is compound no. X.001 [1-(6-chloro-7-methyl-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.002 [4,4-difluoro-1-(6-fluoro-7-methyl-pyrazolo[1,5-a]pyridin-3-yl)-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.003 [1-(6-chloropyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.004 [1-(6-ethylpyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.005 [4,4-difluoro-3,3-dimethyl-1-(6-methylpyrazolo[1,5-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.006 [1-(6-bromopyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.007 [1-(6-bromo-7-methyl-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.008 [1-(6,7-dimethylpyrazolo[1,5-a]pyridin-3-yl)-4,4,5-trifluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.009 [1-(6,7-dimethylpyrazolo[1,5-a]pyridin-3-yl)-4,4,6-trifluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.010 [4,4-difluoro-3,3-dimethyl-1-(7-methylpyrazolo[1,5-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.011 [1-(6,7-dimethylpyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.012 [1-(6,7-dimethylpyrazolo[1,5-a]pyridin-3-yl)-5-fluoro-3,3,4,4-tetramethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.013 [5-fluoro-3,3,4,4-tetramethyl-1-(7-methylpyrazolo[1,5-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.014 [1-(7,8-dimethylimidazo[1,2-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.015 [4,4-difluoro-3,3-dimethyl-1-(7-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.016 [1-(7,8-dimethylimidazo[1,2-a]pyridin-3-yl)-5-fluoro-3,3,4,4-tetramethyl-isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.017 [4,4-difluoro-3,3-dimethyl-1-(8-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.018 [5-fluoro-3,3,4,4-tetramethyl-1-(7-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 20:1 to 1:40.

In another more preferred composition according to the invention component (A) is compound no. X.019 [5-fluoro-3,3,4,4-tetramethyl-1-(8-methylimidazo[1,2-a]pyridin-3-yl)isoquinoline] or a salt, enantiomer, tautomer or N-oxide thereof, and component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil, wherein the weight ratio of component (A) to component (B) is from 10:1 to 1:10.

In a most preferred composition according to the invention component (A) is compound no. X.001 [1-(6-chloro-7-methyl-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.002 [4,4-difluoro-1-(6-fluoro-7-methyl-pyrazolo[1,5-a]pyridin-3-yl)-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.003 [1-(6-chloropyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.004 [1-(6-ethylpyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.005 [4,4-difluoro-3,3-dimethyl-1-(6-methylpyrazolo[1,5-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.006 [1-(6-bromopyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.007 [1-(6-bromo-7-methyl-pyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.008 [1-(6,7-dimethylpyrazolo[1,5-a]pyridin-3-yl)-4,4,5-trifluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.009 [1-(6,7-dimethylpyrazolo[1,5-a]pyridin-3-yl)-4,4,6-trifluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.010 [4,4-difluoro-3,3-dimethyl-1-(7-methylpyrazolo[1,5-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.011 [1-(6,7-dimethylpyrazolo[1,5-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.012 [1-(6,7-dimethylpyrazolo[1,5-a]pyridin-3-yl)-5-fluoro-3,3,4,4-tetramethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.013 [5-fluoro-3,3,4,4-tetramethyl-1-(7-methylpyrazolo[1,5-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.014 [1-(7,8-dimethylimidazo[1,2-a]pyridin-3-yl)-4,4-difluoro-3,3-dimethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.015 [4,4-difluoro-3,3-dimethyl-1-(7-methylimidazo[1,2-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.016 [1-(7,8-dimethylimidazo[1,2-a]pyridin-3-yl)-5-fluoro-3,3,4,4-tetramethyl-isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.017 [4,4-difluoro-3,3-dimethyl-1-(8-methylimidazo[1,2-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.018 [5-fluoro-3,3,4,4-tetramethyl-1-(7-methylimidazo[1,2-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

In another most preferred composition according to the invention component (A) is compound no. X.019 [5-fluoro-3,3,4,4-tetramethyl-1-(8-methylimidazo[1,2-a]pyridin-3-yl)isoquinoline] or a salt, enantiomer, tautomer or N-oxide thereof, and component (B) is a compound selected from the group consisting of Pydiflumetofen, Difenoconazole, Azoxystrobin, Fludioxonil, Cyprodinil and Pyroquilon, wherein the weight ratio of component (A) to component (B) is from 10:1 to 1:10.

Preferred ratios of compounds of formula (I) described in Table X (above) [as component (A)]: mixing partner [component (B)] are given in the Table below for certain preferred mixing partners:

| Mixing partner [component (B)] | Preferred ratio of a compound of formula (I) from Table X (A):mixing partner (B) |
| --- | --- |
| Pydiflumetofen | 5:1 to 1:5 |
| Benzovindiflupyr | 5:1 to 1:5 |
| Difenoconazole | 5:1 to 1:5 |
| Hexaconazole | 3:1 to 1:12 |
| Azoxystrobin | 5:1 to 1:5 |
| Fludioxonil | 2:1 to 1:5 |
| Cyprodinil | 5:1 to 1:5 |
| Isopyrazam | 5:1 to 1:5 |
| Pyroquilon | 1:10 to 1:20 |
| Tricyclazol | 5:1 to 1:5 |
| Chlorothalonil | 1:2 to 1:20 |
| Sulfur | 1:2 to 1:20 |
| Propiconazole | 5:1 to 1:5 |
| *Bacillus subtilis* var. *amyloliquefaciens* Strain FZB24 (Taegro ®) | 5:1 to 1:5 |

According to this disclosure, in a fungicidal compositions comprising a mixture of components (A) and (B), the weight ratio of component (A) to component (B) may be from 100:1 to 1:100, 50:1 to 1:50 and 40:1 to 1:40.

The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

The term "plants" refers to all physical parts of a plant, including seeds, seedlings, saplings, roots, tubers, stems, stalks, foliage, and fruits.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The term "locus" as used herein means fields in or on which plants are growing, or where seeds of cultivated plants are sown, or where seed will be placed into the soil. It includes soil, seeds, and seedlings, as well as established vegetation.

Throughout this document the expression "composition" stands for the various mixtures or combinations of components (A) and (B) (including the above-defined embodiments), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The composition according to the invention is effective against harmful microorganisms, such as microorganisms, that cause phytopathogenic diseases, in particular against phytopathogenic fungi and bacteria.

The composition of the invention may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

The composition is effective in controlling a broad spectrum of plant diseases, such as foliar pathogens of ornamental, turf, vegetable, field, cereal, and fruit crops.

These pathogens may include:

Oomycetes, including *Phytophthora* diseases such as those caused by *Phytophthora capsici, Phytophthora infestans, Phytophthora sojae, Phytophthora fragariae, Phytophthora nicotianae, Phytophthora cinnamomi, Phytophthora citricola, Phytophthora citrophthora* and *Phytophthora erythroseptica*; *Pythium* diseases such as those caused by *Pythium aphanidermatum, Pythium arrhenomanes, Pythium graminicola, Pythium irregulare* and *Pythium ultimum*; diseases caused by Peronosporales such as *Peronospora destructor, Peronospora parasitica, Plasmopara viticola, Plasmopara halstedii, Pseudoperonospora cubensis, Albugo candida, Sclerophthora macrospora* and *Bremia lactucae*; and others such as *Aphanomyces cochlioides, Labyrinthula zosterae, Peronosclerospora sorghi* and *Sclerospora graminicola*;

Ascomycetes, including blotch, spot, blast or blight diseases and/or rots for example those caused by Pleosporales such as *Stemphylium solani, Stagonospora tainanensis, Spilocaea oleaginea, Setosphaeria turcica, Pyrenochaeta lycoperisici, Pleospora herbarum, Phoma destructiva, Phaeosphaeria herpotrichoides, Phaeocryptocus gaeumannii, Ophiosphaerella graminicola, Ophiobolus graminis, Leptosphaeria maculans, Hendersonia creberrima, Helminthosporium triticirepentis, Setosphaeria turcica, Drechslera glycines, Didymella bryoniae, Cycloconium oleagineum, Corynespora cassiicola, Cochliobolus sativus, Bipolaris cactivora, Venturia inaequalis, Pyrenophora teres, Pyrenophora tritici-repentis, Alternaria alternata, Alternaria brassicicola, Alternaria solani* and *Alternaria tomatophila*, Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycovellosiella koepkeii, Phaeoisariopsis bataticola, Pseudocercospora vitis, Pseudocercosporella herpotrichoides, Ramularia beticola, Ramularia collo-cygni*, Magnaporthales such as *Gaeumannomyces graminis, Magnaporthe grisea, Pyricularia oryzae*, Diaporthales such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma*, and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petrieffidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor; Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis*; powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata* and *Oidium arachidis*; molds for example those caused by Botryosphaeriales such as *Dothiorella aromatica, Dipodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum*;

anthracnoses for example those caused by Glommerelales such as *Colletotrichum gloeosporioides, Colletotrichum lagenarium, Colletotrichum gossypii, Glomerella cingulata,* and *Colletotrichum graminicola*; and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f.sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum,* and *Verticillium theobromae;*

Basidiomycetes, including smuts for example those caused by Ustilaginales such as *Ustilaginoidea virens, Ustilago nuda, Ustilago tritici, Ustilago zeae,* rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f.sp. *Hordei, Puccinia striiformis* f.sp. *Secalis, Pucciniastrum coryli,* or Uredinales such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries;*

Blastocladiomycetes, such as *Physoderma maydis;*

Mucoromycetes, such as *Choanephora cucurbitarum.; Mucor* spp.; *Rhizopus arrhizus;* as well as diseases caused by other species and genera closely related to those listed above.

In addition to their fungicidal activity, the compositions may also have activity against bacteria such as *Erwinia amylovora, Erwinia caratovora, Xanthomonas campestris, Pseudomonas syringae, Strptomyces scabies* and other related species as well as certain protozoa.

The composition according to the invention is particularly effective against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgraSciences, Pioneer Hi-Bred International).

Preferred examples of compositions according to the invention are as follows (wherein the term "TX1" represents a compound selected from compound no. X.001, X.002, X.003, X.004, X.005, X.006, X.007, X.008, X.009, X.010, X.011, X.012, X.013, X.014, X.015, X.016, X.017, X.018, X.019 as defined in the Table X above):

TX1+pydiflumetofen, TX1+benzovindiflupyr, TX1+Difenoconazole, TX1+Hexaconazole, TX1+Azoxystrobin, TX1+Fludioxonil, TX1+Cyprodinil, TX1+Fluazinam, TX1+Isopyrazam, TX1+Pyroquilon, TX1+Tricyclazole, TX1+Chlorothalonil, TX1+Propiconazole, TX1+Penconazole, TX1+Fenpropimorph, TX1+Fenpropidin, TX1+Sulfur, TX1+*Bacillus subtilis* var. amyloliquefaciens Strain FZB24 (available from Novozymes Biologicals Inc., 5400 Corporate Circle, Salem, Va. 24153, U.S.A. and known under the trade name Taegro®), wherein the weight ratio of component (A) [TX1] to component (B)[partner] is from 20:1 to 1:40.

The compounds of formula (I) can be made as shown in the following schemes 1 to 17, in which, unless otherwise stated, the definition of each variable is as defined above for a compound of formula (I).

The compounds of formula I-1, wherein $R_1$, $R_2$, $R_3$, $R_4$, $R_5$ and $R_6$ are as defined for compounds of formula (I), can be obtained by transformation of a compound of formula II, wherein $R_5$ and $R_6$ are as defined for compounds of formula (I), with a compound of formula III, wherein $R_1$, $R_2$, $R_3$ and $R_4$ are as defined for compounds of formula (I), under acidic conditions, e.g. with sulphuric acid, trifluoroacetic acid or trifluoromethansulfonic acid. This is shown in Scheme 1.

Compounds of formula III can be obtained by a variety of known methods, e.g. by addition of a Grignard reagent onto the corresponding phenyl acetic esters (see for example: Journal of the American Chemical Society, 1989, 111(12), 4392-8).

Scheme 1

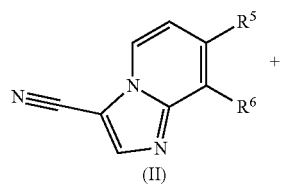

(II)

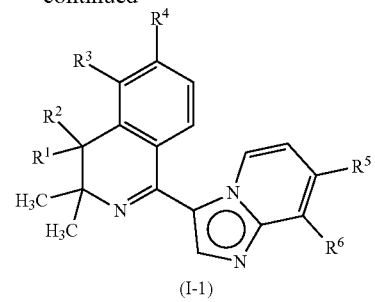

(I-1)

The compounds of formula II, wherein $R_5$ and $R_6$ are as defined for compounds of formula I, can be obtained by transformation of an aminopyridine of formula IV (which are commercially available or obtainable by a variety of known methods), wherein $R_5$ and $R_6$ are as defined for compounds of formula I, with a compound of formula V (which is commercially available or obtainable by a variety of known methods), under oxidative conditions, e.g. with Iodobenzene 1,1-diacetate. Alternatively, the compounds of formula II, wherein $R_5$ and $R_6$ are as defined for compounds of formula I, can be obtained by transformation of an amidine of formula VI (which are commercially available or obtainable by a variety of known methods), wherein $R_5$ and $R_6$ are as defined for compounds of formula I, with a compound of formula VII (which are commercially available or obtainable by a variety of known methods), wherein Hal is a halogen, preferably chloro or bromo, under basic conditions, e.g. with sodium carbonate. This is shown in Scheme 2.

Scheme 2

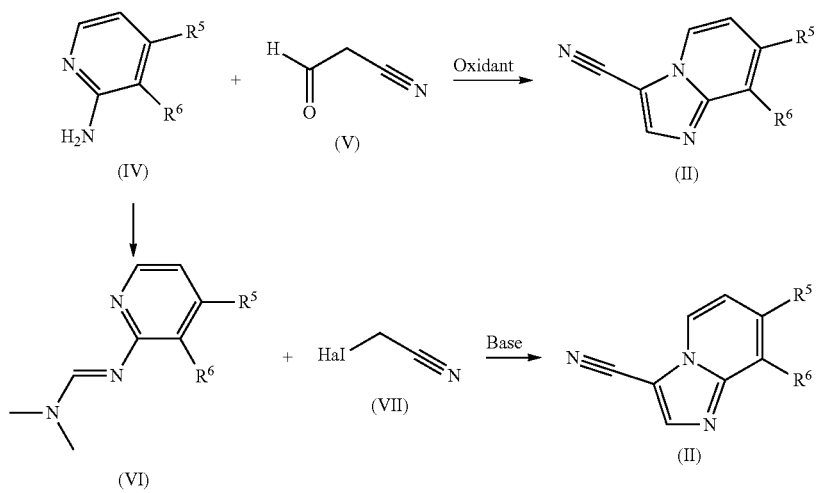

-continued

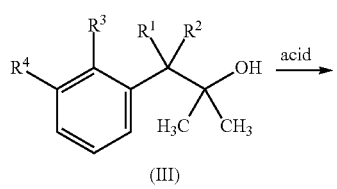

(III)

The compounds of formula I-1, wherein $R_1$, $R_2$, $R_3$, $R_4$, $R_5$ and $R_6$ are as defined for compounds of formula I, can also be obtained by transformation of a compound of formula VIII, wherein $R_5$ and $R_6$ are as defined for compounds of formula (I) and $R_8$ is hydroxyl or two $R^8$ together with the interjacent boron atom form a five- or six-membered saturated heterocyclic ring, with a compound of formula IX, wherein $R_1$, $R_2$, $R_3$ and $R_4$ are as defined for compounds of formula (I) and Hal is halogen, preferably chloro or bromo, under conditions of the Suzuki-Miyaura reaction. This is shown in Scheme 3.

Compounds of formula VIII can be prepared by known methods (see for example: Eur. J. Org. Chem. 2011, 24, 4654 or in Tetrahedron 2008, 64, 4596).

Scheme 3

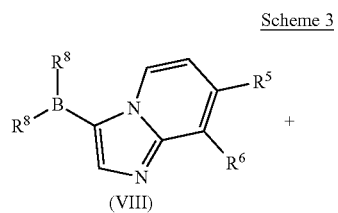

(VIII)

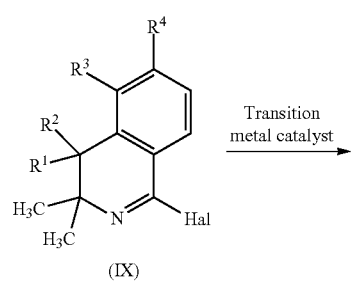

(IX)

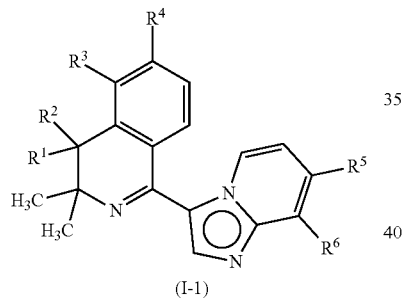

(I-1)

The compounds of formula IX, wherein $R_1$, $R_2$, $R_3$ and $R_4$ are as defined for compounds of formula (I) and Hal is halogen, preferably chloro or bromo, can be obtained by transformation of a compound of formula X, wherein $R_1$, $R_2$, $R_3$ and $R_4$ are as defined for compounds of formula I, with a halogenation reagent, such as phosphorus oxychloride, phosphorus oxybromide, thionyl chloride, thionyl bromide or Vilsmeier reagent. This is shown in Scheme 4.

Scheme 4

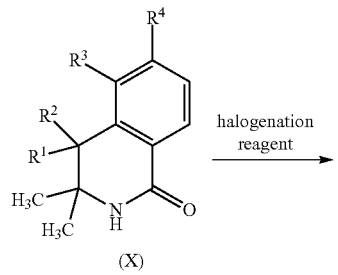

(X)

-continued

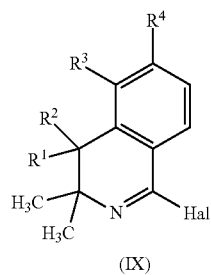

(IX)

Examples of intermediates of formula IX are:

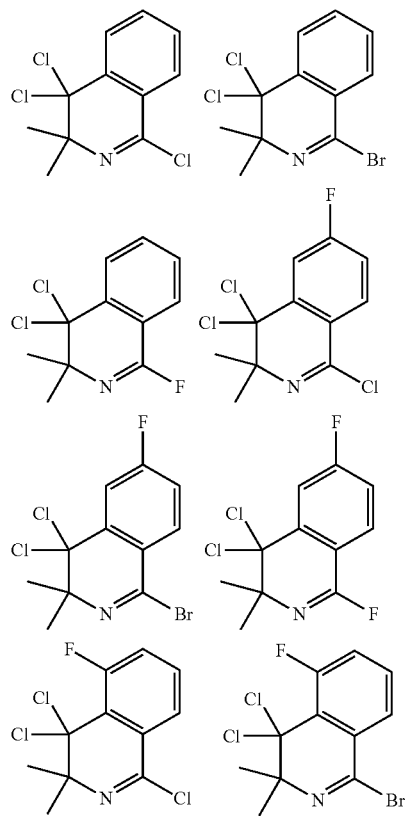

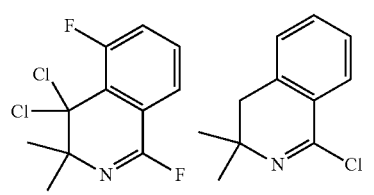

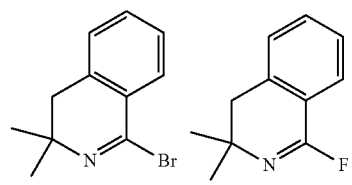

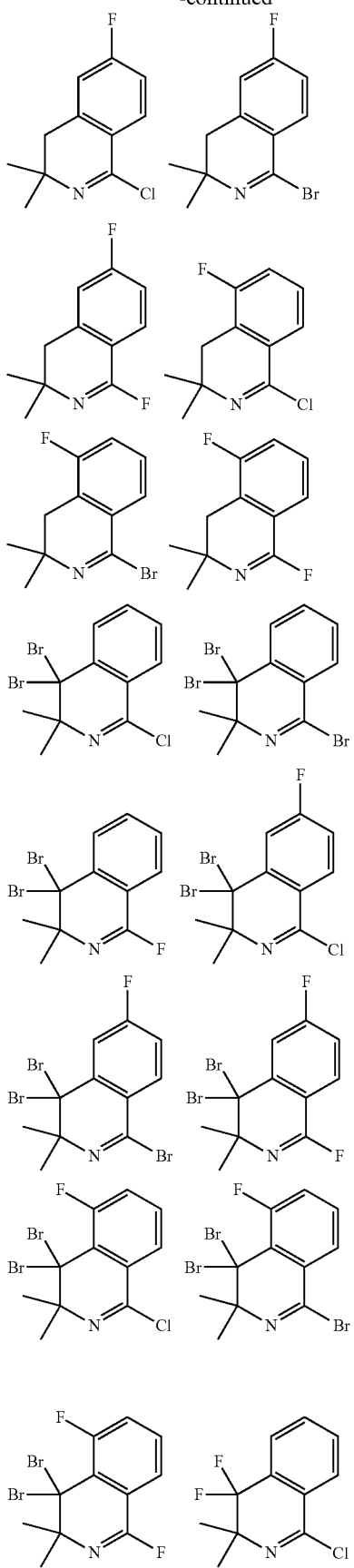

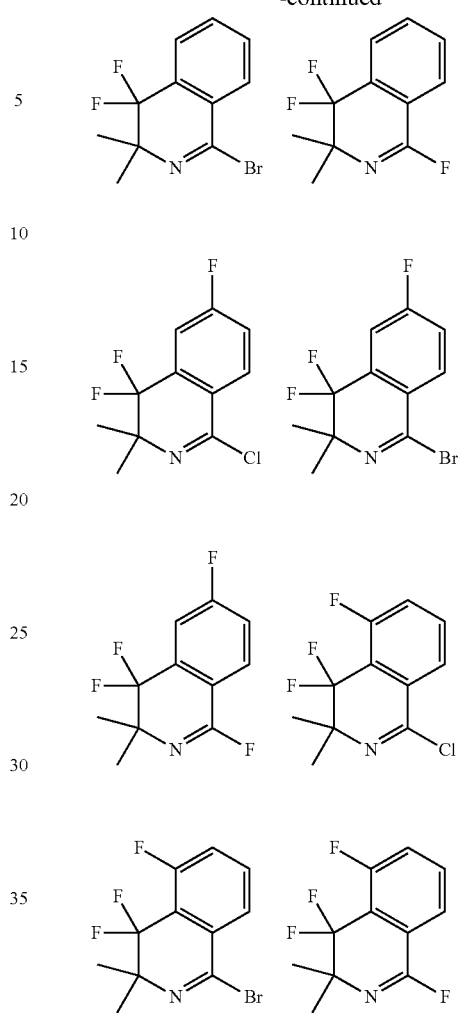

The compounds of formula X, wherein $R_1$, $R_2$, $R_3$ and $R_4$ are as defined for compounds of formula I, can be obtained by several transformation known to the person skilled in the art, for instance they can be prepared by transformation of a compound of formula XI, wherein $R_1$, $R_2$, $R_3$ and $R_4$ are as defined for compounds of formula (I) and $R_9$ is $C_1$-$C_6$ alkyl, with sodium acetate in acetic acid acid as described in the literature (Yu. B. Vikharev et al. Pharmaceutical Chemistry Journal, 2005, 39, 405-408). This is shown in Scheme 5.

Scheme 5

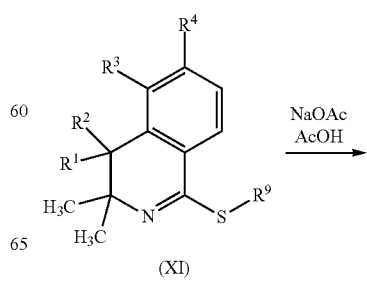

(XI)

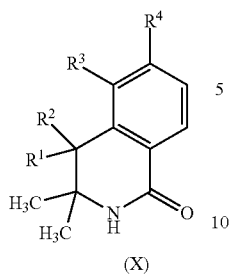

Examples of intermediates of formula X are:

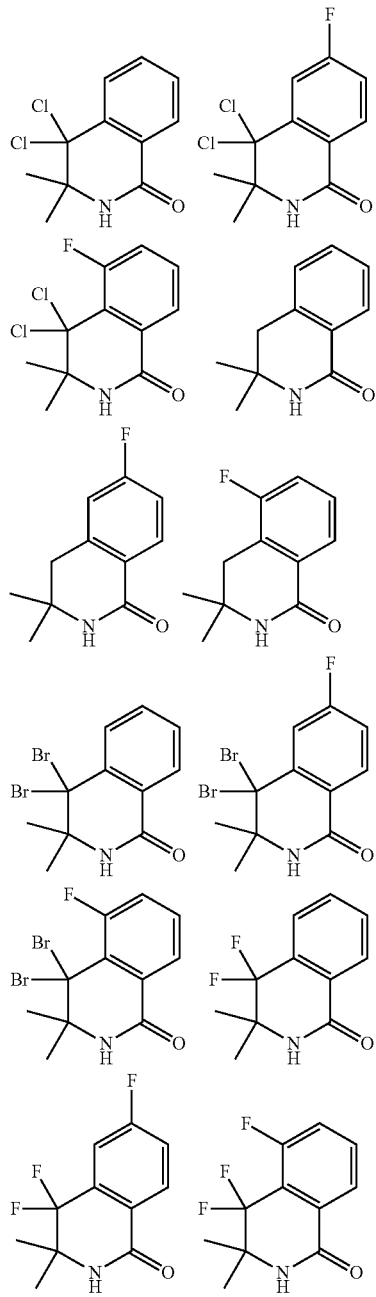

The compounds of formula XI, wherein $R_1$, $R_2$, $R_3$ and $R_4$ are as defined for compounds of formula (I) and $R_9$ is $C_1$-$C_6$ alkyl, can be obtained by transformation of a compound of formula III-a, III-b or III-c, wherein $R_1$, $R_2$, $R_3$ and $R_4$ are as defined for compounds of formula (I) and R' is either H or $C_1$-$C_6$ alkyl, with a $C_1$-$C_6$ alkyl thiocyanate under acidic conditions, e.g. with sulfuric acid as described in the literature (Yu. B. Vikharev et al. Pharmaceutical Chemistry Journal, 2005, 39, 405-408). This is shown in Scheme 6.

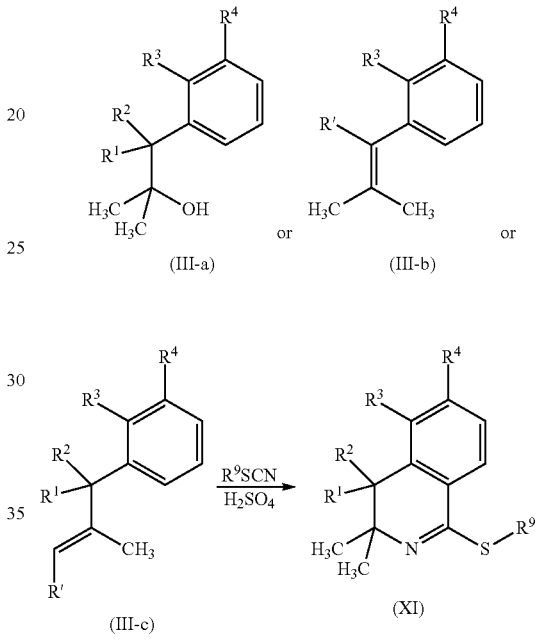

The compounds of formula I-2, wherein $R_1$, $R_2$, $R_3$, $R_4$, $R_5$ and $R_6$ are as defined for compounds of formula I, can be obtained by transformation of a compound of formula XVII, wherein $R_5$ and $R_6$ are as defined for compounds of formula I, with a compound of formula III, wherein $R_1$, $R_2$, $R_3$ and $R_4$ are as defined for compounds of formula I, under acidic conditions, e.g. with sulphuric acid, trifluoroacetic acid or trifluoromethansulfonic acid. This is shown in Scheme 7.

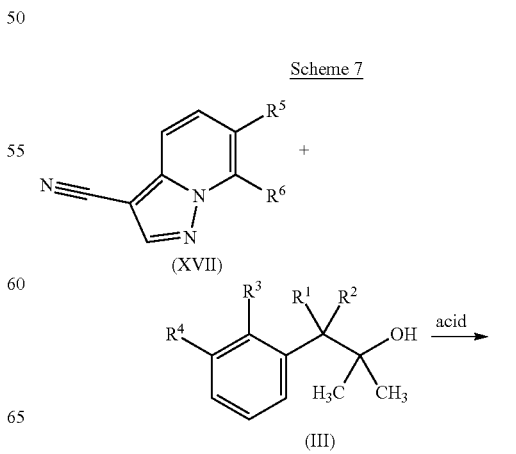

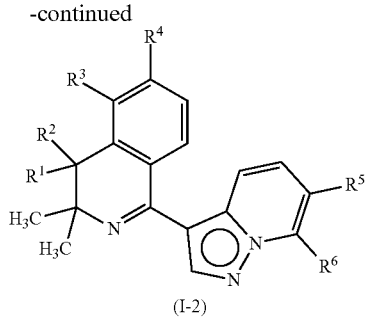

(I-2)

The compounds of formula XVII wherein $R_5$ and $R_6$ are as defined for compounds of formula (I) can be obtained by known methods (see, for example: A. Kakehi et al *Chemical & Pharmaceutical Bulletin,* 1987, 35, 156-169; P. Gmeiner and J. Schunemann *Archiv de Pharmazie* 1988, 321, 517-20). As an example, compounds XVII can be prepared by reaction of 3-methoxyprop-2-enenitrile with N-amino pyridinium salts of formula XVIII (which are commercially available or can be obtained by known methods) wherein $R_5$ and $R_6$ are as defined for formula (I) and the anion $A^-$ can be of different nature (e. g. iodide or 2,4,6-trimethylbenzenesulfonate), in the presence of a base, e. g. with potassium carbonate. This is shown in Scheme 8.

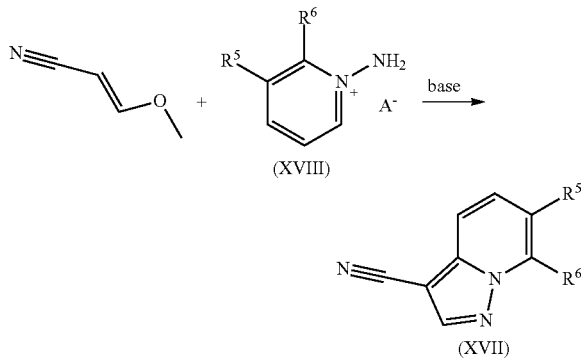

Alternatively, the compounds of formula I-2, wherein $R_1$, $R_2$, $R_3$, $R_4$, $R_5$ and $R_6$ are as defined for compounds of formula I, can be obtained by treatment of a compound of formula IX-c, wherein $R_1$, $R_2$, $R_3$ and $R_4$ are as defined for compounds of formula I, with a compound of formula XVIII, wherein $A^-$ is as defined in scheme 8, $R_5$ and $R_6$ are as defined for compounds of formula I, in the presence of a base such as potassium carbonate in inert solvent such as dimethylformamide. This is shown in Scheme 9.

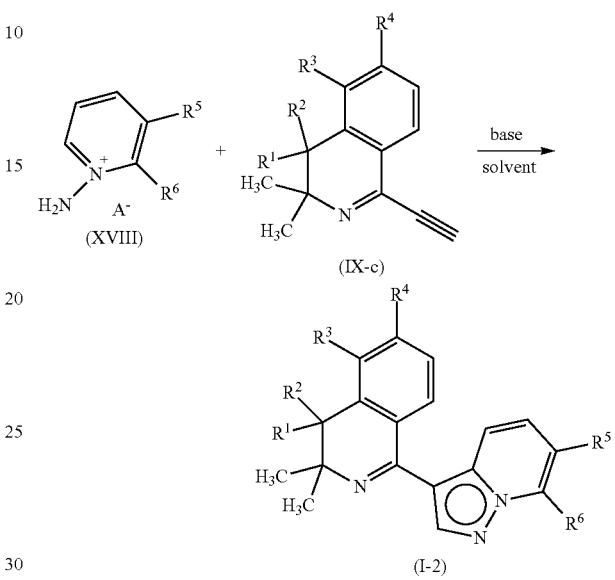

The compounds of formula IX-c, wherein $R_1$, $R_2$, $R_3$ and $R_4$ are as defined for compounds of formula I, can be obtained by treatment of a compound of formula IX, wherein $R_1$, $R_2$, $R_3$ and $R_4$ are as defined for compounds of formula (I) and Hal is halogen, preferably chloro or bromo, with a compound of formula XXI under conditions of the Sonogashira reaction. For compounds of formula IX-c, wherein $R_1$, $R_2$, $R_3$ and $R_4$ are as defined for compounds of formula (I), the Sonogashira reaction described above is preferably performed with compounds of formula XXII, wherein $R_{10}$ is $C_1$-$C_6$ alkyl, to yield compounds of formula IX-d, wherein $R_1$, $R_2$, $R_3$ and $R_4$ are as defined for compounds of formula (I) and $R_{10}$ is $C_1$-$C_6$ alkyl, followed by desilylation under conditions well known to a person skilled in the art such as possium carbonate in an alcohol solvents such as methanol. This is shown in Scheme 10.

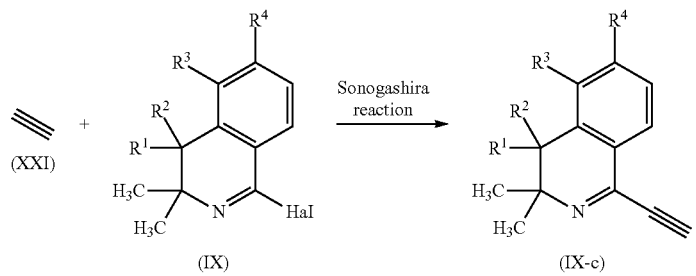

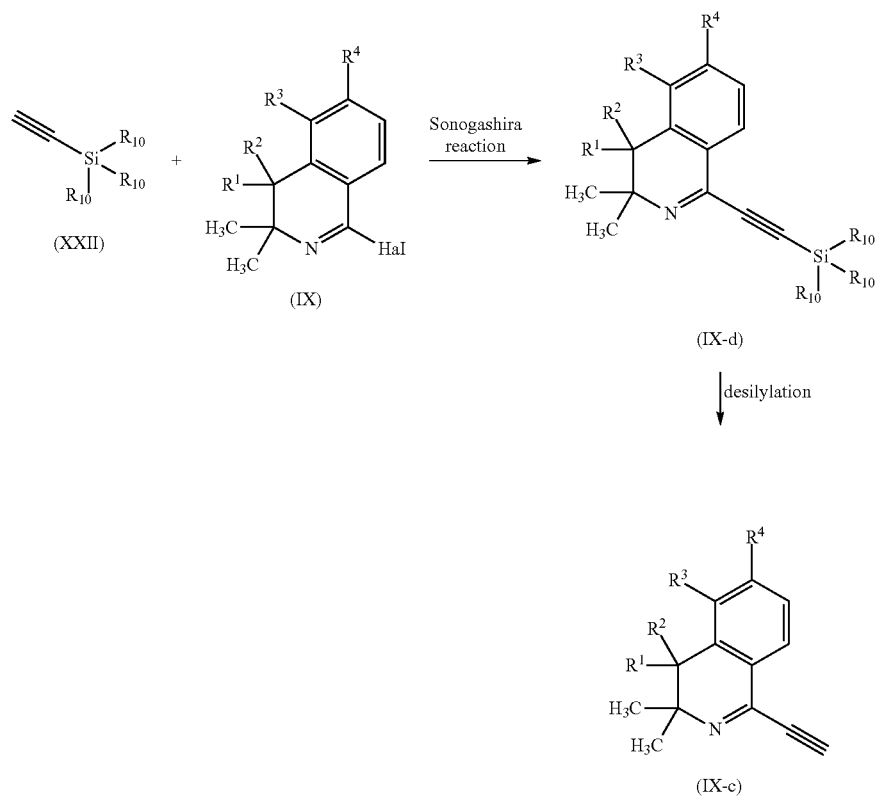

The compounds of formula I-c, wherein $R_1$ and $R_2$ are fluoro and $Q_1$, $Q_2$, $R_3$, $R_4$, $R_5$ and $R_6$ are as defined for compounds of formula I, can be obtained by transformation of a compound of formula I-d wherein $R_1$ and $R_2$ together with the carbon atom to which they are attached represent C=O and $Q_1$, $Q_2$, $R_3$, $R_4$, $R_5$ and $R_6$ are as defined for formula (I) with a fluorinating agent such as diethylaminosulfur trifluoride (DAST) or 2,2-difluoro-1,3-dimethyl-imidazolidine (DFI) neat or in the presence of a solvent while heating. This is shown in Scheme 11.

Scheme 11

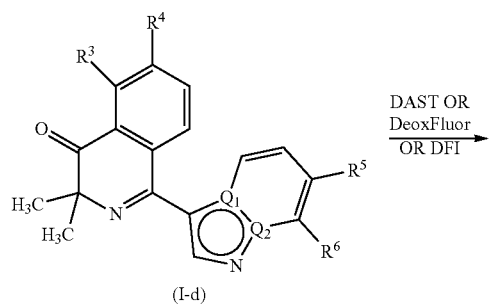

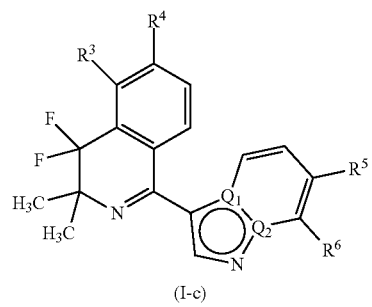

The compounds of formula I-d wherein $R_1$ and $R_2$ together with the carbon atom to which they are attached represent C=O and $Q_1$, $Q_2$, $R_3$, $R_4$, $R_5$ and $R_6$ are as defined for formula I, can be obtained by transformation of a compound of formula I-e wherein $R^1$ is hydrogen and $R^2$ is hydroxy and $Q_1$, $Q_2$, $R_3$, $R_4$, $R_5$ and $R_6$ are as defined for formula (I) with an oxidizing agent such as 1,1,1-triacetoxy-1,1-dihydro-1,2-benziodoxol3(1H)-one (Dess-Martin periodinane) or using oxalyl chloride, dimethyl sulfoxide (DMSO) and an organic base, such as triethylamine (Swern oxidation). This is shown in Scheme 12.

Scheme 12

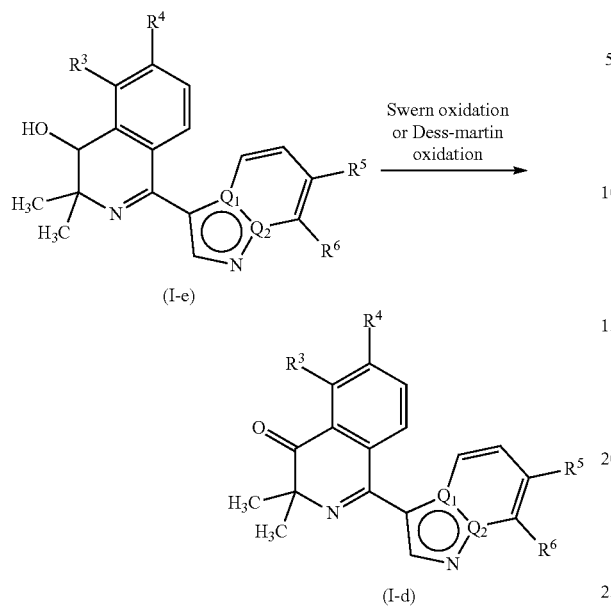

The compounds of formula I-e wherein $R_1$ is hydrogen and the $R_2$ position is hydroxy and $Q_1$, $Q_2$, $R_3$, $R_4$, $R_5$ and $R_6$ are as defined for formula I, can be obtained by transformation of a compound of formula I-f wherein $R_1$ is hydrogen and $R_2$ is halogen (Hal) such as bromo or chloro and $Q_1$, $Q_2$, $R_3$, $R_4$, $R_5$ and $R_6$ are as defined for formula (I) under hydrolysis condition such as aqueous $K_2CO_3$. This is shown in Scheme 13.

Scheme 13

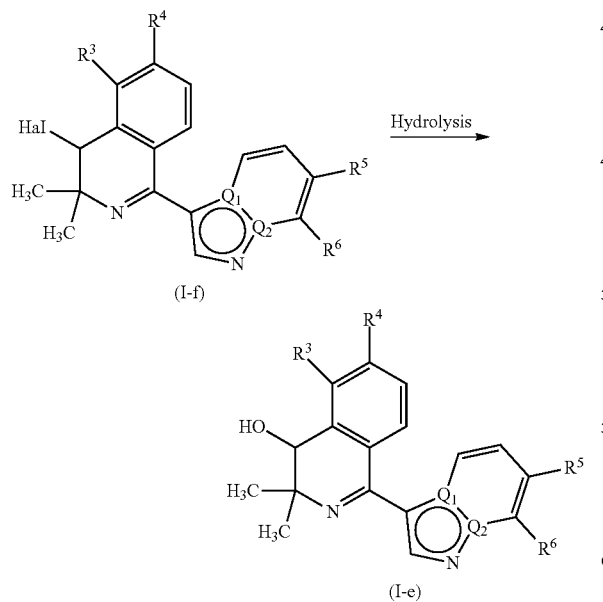

The compound of formula I-f wherein $R_1$ is hydrogen and $R_2$ is halogen (hal) such as bromo or chloro and $Q_1$, $Q_2$, $R_3$, $R_4$, $R_5$ and $R_6$ are as defined for formula I, can be obtained by transformation of a compound of formula I-g wherein $R^1$ and $R^2$ are hydrogen and $Q_1$, $Q_2$, $R_3$, $R_4$, $R_5$ and $R_6$ are as defined for formula (I) with an halogenating agent such as N-bromo succinimide (NBS) or N-chloro succinimide or 1,3-dibromo-5,5-dimethylhydantoin in the presence of a radical initiator such as azobisisobutyronitrile (AIBN). This is shown in Scheme 14.

Scheme 14

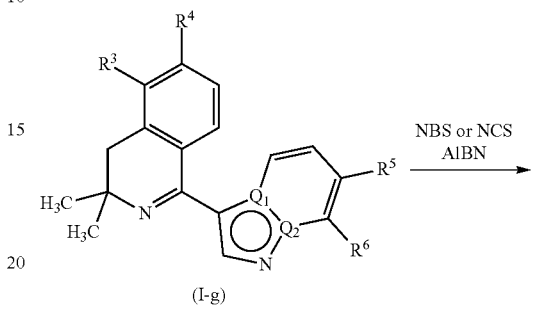

Alternatively, the compounds of formula I-d wherein $R_1$ and $R_2$ together with the carbon atom to which they are attached represent C=O and $R_3$, $R_4$, $R_5$ and $R_6$ are as defined for formula I, can be obtained by treatment of a compound of formula IX-i, wherein $R_1$ and $R_2$ together with the carbon atom to which they are attached represent C=O and $R_3$ and $R_4$ are as defined for compounds of formula (I), with a compound of formula XVIII, wherein $A^-$ is as defined in scheme 8, $R_5$ and $R_6$ are as defined for compounds of formula I, in the presence of a base such as potassium carbonate in inert solvent such as dimethylformamide. This is shown in scheme 15.

Scheme 15

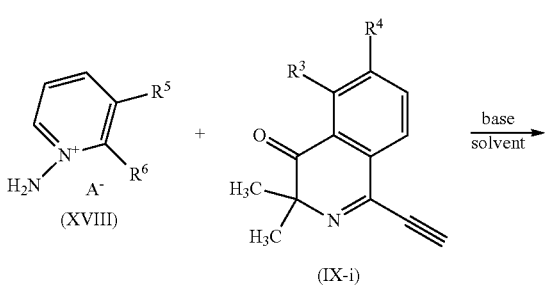

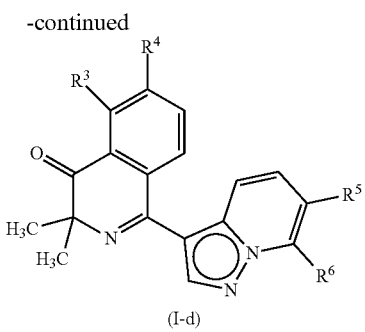

(I-d)

The compounds of formula IX-i, wherein $R_1$ and $R_2$ together with the carbon atom to which they are attached represent C=O and $R_3$ and $R_4$ are as defined for compounds of formula (I) can be obtained by treatment of a compound of formula IX-w (refer WO 2016/156085), wherein $R_1$ and $R_2$ together with the carbon atom to which they are attached represent C=O, $R_3$ and $R_4$ are as defined for compounds of formula (I) and Hal is halogen, preferably chloro or bromo, with a compound of formula XXI under conditions of the Sonogashira reaction. For compounds of formula IX-i, wherein $R_1$ and $R_2$ together with the carbon atom to which they are attached represent C=O and $R_3$ and $R_4$ are as defined for compounds of formula (I), the Sonogashira reaction described above is preferably performed with compounds of formula XXII, wherein $R_{10}$ is $C_1$-$C_6$ alkyl, to yield compounds of formula IX-z wherein $R_1$ and $R_2$ together with the carbon atom to which they are attached represent C=O, $R_3$ and $R_4$ are as defined for compounds of formula (I) and $R_{10}$ is $C_1$-$C_6$ alkyl, followed by desilylation under conditions well known to a person skilled in the art such as possium carbonate in an alcohol solvents such as methanol. This is shown in Scheme 16.

Scheme 16

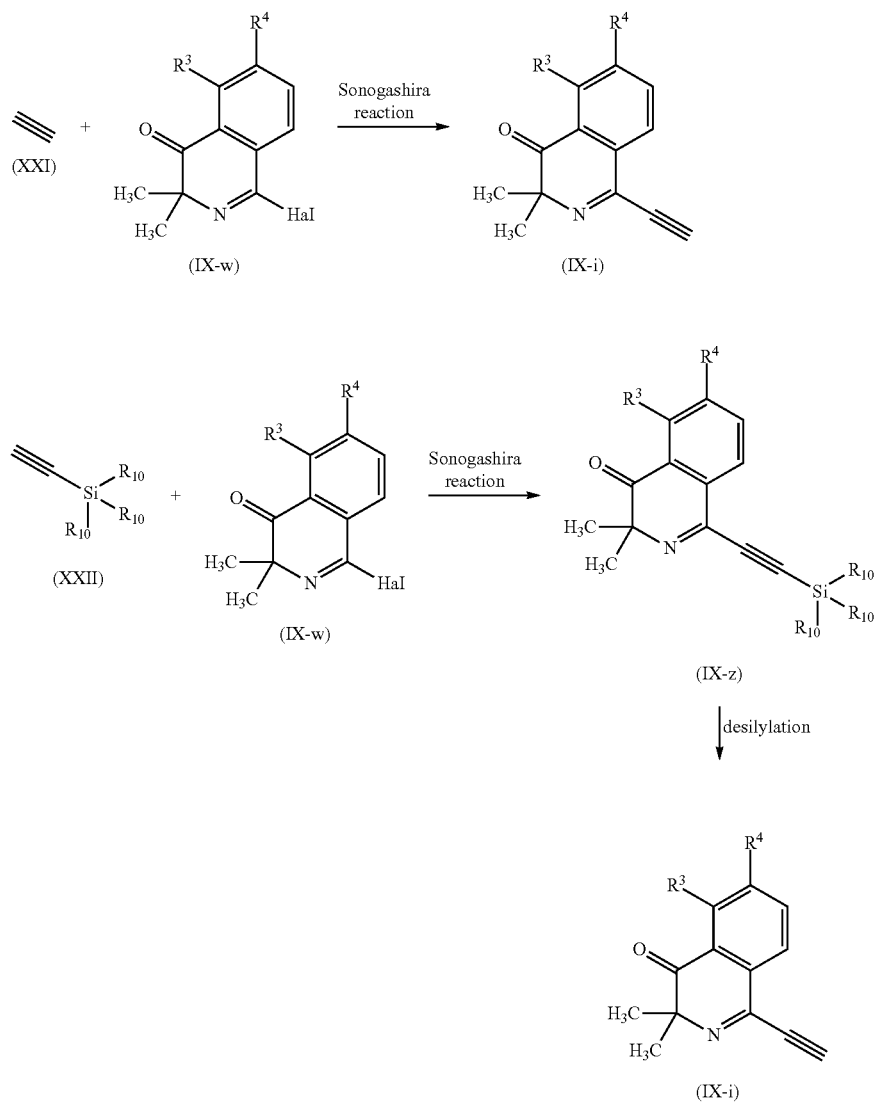

Alternatively, the compounds of formula I, wherein $Q_1$, $Q_2$, $R_1$, $R_2$, $R_3$, $R_4$, $R_5$ and $R_6$ are as defined for compounds of formula I, can be obtained by transformation of a compound of formula I-i, wherein $Q_1$, $Q_2$, $R_1$, $R_2$, $R_3$ and $R_4$ are as defined for compounds of formula (I) and Y represents chlorine, bromine or iodine in a solvent, in the presence of or absence of a base, and in the presence of a coupling reagent and a metal catalyst. There are no particular limitations on the coupling agent, catalyst, solvent and bases, provided it is used in ordinary coupling reactions, such as those described in "Cross-Coupling Reactions: A Practical Guide (Topics in Current Chemistry)", edited by Norio Miyaura and S. L. Buchwald (editions Springer), or "Metal-Catalyzed Cross-Coupling Reactions", edited by Armin de Meijere and François Diederich (editions WILEY-VCH). This is shown in Scheme 17.

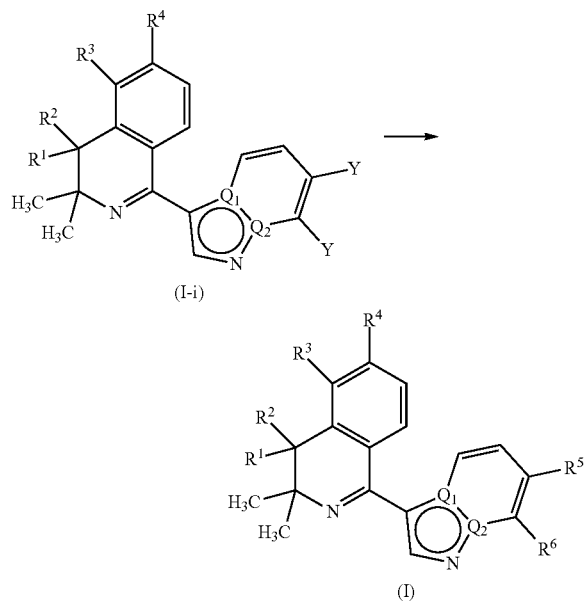

Scheme 17

The compounds of formula (I) wherein $Q_1$, $Q_2$, $R_1$, $R_2$, $R_3$, $R_4$, $R_5$ and $R_6$ are as defined above, can be obtained by transformation of another, closely related, compound of formula (I) (or an analogue thereof) using standard synthesis techniques known to the person skilled in the art. Non-exhaustive examples include oxidation reactions, reduction reactions, hydrolysis reactions, coupling reactions, aromatic nucleophilic or electrophilic substitution reactions, nucleophilic substitution reactions, nucleophilic addition reactions, and halogenation reactions.

Compositions of this invention, including all of the above disclosed embodiments and preferred examples thereof, can be mixed with one or more further pesticides including further fungicides, insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection.

Examples of such agricultural protectants with which the composition of this invention can be formulated are:

Fungicides such as etridiazole, fluazinam, benalaxyl, benalaxyl-M (kiralaxyl), furalaxyl, metalaxyl, metalaxyl-M (mefenoxam), dodicin, N'-(2,5-Dimethyl-4-phenoxy-phenyl)-N-ethyl-N-methyl-formamidine, N'-[4-(4,5-Dichloro-thiazol-2-yloxy)-2,5-dimethyl-phenyl]-N-ethyl-N-methyl-formamidine, N'-[4-[[3-[(4-chlorophenyl)methyl]-1,2,4-thiadiazol-5-yl]oxy]-2,5-dimethyl-phenyl]-N-ethyl-N-methyl-formamidine, ethirimol, 3'-chloro-2-methoxy-N-[(3RS)-tetrahydro-2-oxofuran-3-yl]acet-2',6'-xylidide (clozylacon), cyprodinil, mepanipyrim, pyrimethanil, dithianon, aureofungin, blasticidin-S, biphenyl, chloroneb, dicloran, hexachlorobenzene, quintozene, tecnazene, (TCNB), tolclofos-methyl, metrafenone, 2,6-dichloro-N-(4-trifluoromethylbenzyl)-benzamide, fluopicolide (flupicolide), tioxymid, flusulfamide, benomyl, carbendazim, carbendazim chlorhydrate, chlorfenazole, fuberidazole, thiabendazole, thiophanate-methyl, benthiavalicarb, chlobenthiazone, probenazole, acibenzolar, bethoxazin, pyriofenone (IKF-309), acibenzolar-S-methyl, pyribencarb (KIF-7767), butylamine, 3-iodo-2-propinyl n-butylcarbamate (IPBC), iodocarb (isopropanyl butylcarbamate), isopropanyl butyl-carbamate (iodocarb), picarbutrazox, polycarbamate, propamocarb, tolprocarb, 3-(difluoromethyl)-N-(7-fluoro-diclocymet, N-[(5-chloro-2-isopropyl-phenyl)methyl]-N-cyclopropyl-3-(difluoromethyl)-5-fluoro-1-methyl-pyrazole-4-carboxamide N-cyclopropyl-3-(difluoromethyl)-5-fluoro-N-[(2-isopropylphenyl)methyl]-1-methyl-pyrazole-4-carboxamide carpropamid, chlorothalonil, flumorph, oxine-copper, cymoxanil, phenamacril, cyazofamid, flutianil, thicyofen, chlozolinate, iprodione, procymidone, vinclozolin, bupirimate, dinocton, dinopenton, dinobuton, dinocap, meptyldinocap, diphenylamine, phosdiphen, 2,6-dimethyl-[1,4]dithiino[2,3-c:5,6-c']dipyrrole-1,3,5,7(2H,6H)-tetraone, azithiram, etem, ferbam, mancozeb, maneb, metam, metiram (polyram), metiram-zinc, nabam, propineb, thiram, vapam (metam sodium), zineb, ziram, dithioether, isoprothiolane, ethaboxam, fosetyl, phosetyl-Al (fosetyl-al), methyl bromide, methyl iodide, methyl isothiocyanate, cyclafuramid, fenfuram, validamycin, streptomycin, (2RS)-2-bromo-2-(bromomethyl)glutaronitrile (bromothalonil), dodine, doguadine, guazatine, iminoctadine, iminoctadine triacetate, 2,4-D, 2,4-DB, kasugamycin, dimethirimol, fenhexamid, hymexazole, hydroxyisoxazole imazalil, imazalil sulphate, oxpoconazole, pefurazoate, prochloraz, triflumizole, fenamidone, Bordeaux mixture, calcium polysulfide, copper acetate, copper carbonate, copper hydroxide, copper naphthenate, copper oleate, copper oxychloride, copper oxyquinolate, copper silicate, copper sulphate, copper tallate, cuprous oxide, sulphur, carbaryl, phthalide (fthalide), dingjunezuo (Jun Si Qi), oxathiapiprolin, fluoroimide, mandipropamid, KSF-1002, benzamorf, dimethomorph, fenpropimorph, tridemorph, dodemorph, diethofencarb, fentin acetate, fentin hydroxide, carboxin, oxycarboxin, drazoxolon, famoxadone, m-phenylphenol, p-phenylphenol, tribromophenol (TBP), 2-[2-[(7,8-difluoro-2-methyl-3-quinolyl)oxy]-6-fluoro-phenyl]propan-2-ol 2-[2-fluoro-6-[(8-fluoro-2-methyl-3-quinolyl)oxy]phenyl] propan-2-ol cyflufenamid, ofurace, oxadixyl, flutolanil, mepronil, isofetamid, fenpiclonil, fludioxonil, pencycuron, edifenphos, iprobenfos, pyrazophos, phosphorus acids, tecloftalam, captafol, captan, ditalimfos, triforine, fenpropidin, piperalin, osthol, 1-methylcyclopropene, 4-CPA, chlormequat, clofencet, dichlorprop, dimethipin, endothal, ethephon, flumetralin, forchlorfenuron, gibberellic acid, gibberellins, hymexazol, maleic hydrazide, mepiquat, naphthalene acetamide, paclobutrazol, prohexadione, prohexadione-calcium, thidiazuron, tribufos (tributyl phosphorotrithioate), trinexapac, uniconazole, α-naphthalene acetic acid, polyoxin D (polyoxrim), BLAD, chitosan, fenoxanil, folpet, 3-(difluoromethyl)-N-methoxy-1-methyl-N-[1-methyl-2-(2,4,6-trichlorophenyl)ethyl]pyrazole-4-carboxamide, bixafen, fluxapyroxad, furametpyr, isopyrazam, penflufen, penthiopyrad, sedaxane, fenpyrazamine, diclomezine, pyrifenox, boscalid, fluopyram, diflumetorim, fenarimol, 5-fluoro-2-(p-tolylmethoxy)pyrimidin-4-amine ferimzone, dimetachlone (dimethaclone), pyroquilon, proquinazid, ethoxyquin, quinoxyfen, 4,4,5-trifluoro-3,3-dimethyl-1-(3-quinolyl)isoquinoline, 4,4-difluoro-3,3-dimethyl-1-(3-quinolyl)isoquinoline 5-fluoro-3,3,4,4-tetramethyl-1-(3-quinolyl)isoquinoline 9-fluoro-2,2-dimethyl-5-(3-quinolyl)-3H-1,4-benzoxazepine, tebufloquin, oxolinic acid, chinomethionate (oxythioquinox, quinoxymethionate), spiroxamine, (E)-N-methyl-2-[2-(2,5-dimethylphenoxymethyl) phenyl]-2-methoxy-iminoacetamide, (mandestrobin), azoxystrobin, coumoxystrobin, dimoxystrobin, enestroburin, enoxastrobin fenamistrobin, flufenoxystrobin, fluoxastrobin, kresoxim-methyl, mandestrobin, metaminostrobin, metominostrobin, orysastrobin, picoxystrobin, pyraclostrobin, pyrametostrobin, pyraoxystrobin, triclopyricarb, trifloxystrobin, amisulbrom, dichlofluanid, tolylfluanid, but-3-ynyl N-[6-[[(Z)-[(1-methyltetrazol-5-yl)-phenyl-methylene]amino]oxymethyl]-2-pyridyl]carbamate, dazomet, isotianil, tiadinil, thifluzamide, benthiazole (TCMTB), silthiofam, zoxamide, anilazine, tricyclazole, (.+-.)-cis-1-(4-chlorophenyl)-2-(1H-1,2,4-triazol-1-yl)-cycloheptanol (huanjunzuo), 1-(5-bromo-2-pyridyl)-2-(2,4-difluorophenyl)-1,1-difluoro-3-(1,2,4-triazol-1-yl)propan-2-ol 2-(1-tert-butyl)-1-(2-chlorophenyl)-3-(1,2,4-triazol-1-yl)-propan-2-ol (TCDP), azaconazole, bitertanol (biloxazol), bromuconazole, climbazole, cyproconazole, difenoconazole, dimetconazole, diniconazole, diniconazole-M, epoxiconazole, etaconazole, fenbuconazole, fluquinconazole, flusilazole, flutriafol, hexaconazole, imibenconazole, ipconazole, ipfentrifluconazole, metconazole, myclobutanil, penconazole, propiconazole, prothioconazole, simeconazole, tebuconazole, tetraconazole, triadimefon, triadimenol, triazoxide, triticonazole, Mefentrifluconazole, 2-[[(1R,5S)-5-[(4-fluorophenyl)methyl]-1-hydroxy-2,2-dimethyl-cyclopentyl]methyl]-4H-1,2,4-triazole-3-thione 2-[[3-(2-chlorophenyl)-2-(2,4-difluorophenyl)oxiran-2-yl]methyl]-4H-1,2,4-triazole-3-thione, ametoctradin (imidium), iprovalicarb, valifenalate, 2-benzyl-4-chlorophenol (Chlorphene), allyl alcohol, azafenidin, benzalkonium chloride, chloropicrin, cresol, daracide, dichlorophen (dichlorophene), difenzoquat, dipyrithione, N-(2-p-chlorobenzoylethyl)-hexaminium chloride, NNF-0721, octhilinone, oxasulfuron, propamidine and propionic acid.

Insecticides such as abamectin, acephate, acetamiprid, amidoflumet (S-1955), avermectin, azadirachtin, azinphos-methyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, novifluron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron;

Bactericides such as streptomycin;

Acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and Biological agents such as *Bacillus thuringiensis, Bacillus thuringiensis* delta endotoxin, baculovirus, and entomopathogenic bacteria, virus and fungi.

Other examples of "reference" mixture compositions are as follows (wherein the term "TX" represents a compound selected from compound no. X.001, X.002, X.003, X.004, X.005, X.006, X.007, X.008, X.009, X.010, X.011, X.012, X.013, X.014, X.015, X.016, X.017, X.018, X.019 as defined in the Table X above):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyamino-thiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B2 (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085) +TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin 11 (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetramat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium* verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+

TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, benzovindiflupyr [1072957-71-1]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, ipfentrifluconazole [1417782-08-1]+TX, mefentrifluconazole [1417782-03-6]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoximmethyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fos-etyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pydiflumetofen [1228284-64-7]+TX, pyroquilon [57369-32-1]+TX, quinoxyfen [124495-18-7]+TX, quintozene [82-68-8]+TX, sulfur [7704-34-9]+TX, Timorex Gold' (plant extract containing tea tree oil from the Stockton Group)+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, or a biologically active compound selected from the group consisting of N-[(5-chloro-2-isopropyl-phenyl)methyl]-N-cyclopropyl-3-(difluoromethyl)-5-fluoro-1-methyl-pyrazole-4-carboxamide+TX, 2,6-Dimethyl-1H,5H-[1,4]dithiino[2,3-c:5,6-c]dipyrrole-1,3,5,7(2H,6H)-tetrone+TX, 6-ethyl-5,7-dioxo-pyrrolo[4,5][1,4]dithiino[1,2-c]isothiazole-3-carbonitrile+TX, 4-(2-bromo-4-fluoro-phenyl)-N-(2-chloro-6-fluoro-phenyl)-2,5-dimethyl-pyrazol-3-amine+TX, 3-(difluoromethyl)-N-(7-fluoro-1,1,3-trimethyl-indan-4-yl)-1-methyl-pyrazole-4-carboxamide+TX, CAS 850881-30-0+TX, 3-(3,4-dichloro-1,2-thiazol-5-ylmethoxy)-1,2-benzothiazole 1,1-dioxide+TX, 2-[2-[(2,5-dimethylphenoxy)methyl]phenyl]-2-methoxy-N-methyl-acetamide+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, N-[2-(3,4-difluorophenyl)phenyl]-3-(trifluoromethyl)pyrazine-2-carboxamide+TX, 3-(difluoromethyl)-1-methyl-N-[(3R)-1,1,3-trimethylindan-4-yl]pyrazole-4-carboxamide+TX, 2,2,2-trifluoroethyl N-[2-methyl-1-[[(4-methylbenzoyl)amino]methyl]propyl]carbamate+TX, (2RS)-2-[4-(4-chlorophenoxy)-α,α,α-trifluoro-o-tolyl]-1-(1H-1,2,4-triazol-1-yl)propan-2-ol+TX, (2RS)-2-[4-(4-chlorophenoxy)-α,α,α-trifluoro-o-tolyl]-3-methyl-1-(1H-1,2,4-triazol-1-yl)butan-2-ol+TX, 2-(difluoromethyl)-N-[(3R)-3-ethyl-1,1-dimethyl-indan-4-yl]pyridine-3-carboxamide+TX, 2-(difluoromethyl)-N-[3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl]methanesulfonate+TX, but-3-ynyl N-[6-[[(Z)-[(1-methyltetrazol-5-yl)-phenyl-methylene]amino]oxymethyl]-2-pyridyl]carbamate+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine+TX, 3-chloro-4-(2,6-difluorophenyl)-6-methyl-5-phenyl-pyridazine+TX, 4-(2,6-difluorophenyl)-6-methyl-5-phenyl-pyridazine-3-carbonitrile+TX, 2-[2-[(7,8-difluoro-2-methyl-3-quinolyl)oxy]-6-fluoro-phenyl]propan-2-ol+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, (Z,2E)-5-[1-(4-chlorophenyl)pyrazol-3-yl]oxy-2-methoxyimino-N,3-dimethyl-pent-3-enamide+TX, (4-phenoxyphenyl)methyl 2-amino-6-methyl-pyridine-3-carboxylate+TX, N-[1,1-dimethyl-2-(4-isopropoxy-o-tolyl)-2-oxoethyl]-3-methylthiophene-2-carboxamide+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, N-{[3-chloro-5-(trifluoromethyl)-2-pyridyl]methyl}-2,3,5,6-tetrafluoro-4-methoxybenzamide+TX, [(1S)-2,2-bis(4-fluorophenyl)-1-methyl-ethyl] (2S)-2-[(3-acetoxy-4-methoxy-pyridine-2-carbonyl)amino]propanoate+TX, (Z)—N-{2-[3-chloro-5-(cyclopropylethynyl)-2-pyridyl]-2-(isopropoxyimino)ethyl}-3-(difluoromethyl)-1-methylpyrazole-4-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, and

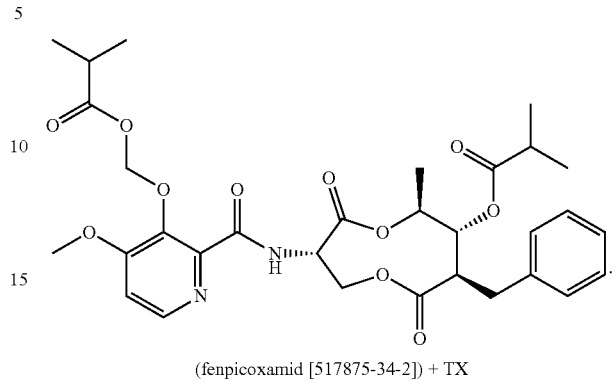

(fenpicoxamid [517875-34-2]) + TX

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

In the "reference" mixture compositions the mixtures of compounds of formula (I) [selected from Table X (above)] with active ingredients described above comprise a compound selected from Table X (above) and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixture compositions as described above (both according to the ivnetion and the "reference" mixture compositions) can be used in a method for controlling pests, which comprises applying a composition comprising a mixture as described above to the pests or their environment.

The mixtures comprising a compound of formula (I) selected from Table X (above) and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Table X (above) and the active ingredients as described above is not essential for working the present invention.

The compositions of the present invention may also be used in crop enhancement.

According to the present invention, 'crop enhancement' means an improvement in plant vigour, an improvement in plant quality, improved tolerance to stress factors, and/or improved input use efficiency.

According to the present invention, an 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

According to the present invention, an 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

According to the present invention, an 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

According to the present invention, an 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other crop enhancements of the present invention include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compositions of the present invention may also be used in the field of protecting storage goods against attack of fungi. According to the present invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The composition according the present invention can prevent disadvantageous effects such as decay, discoloration or mold. Preferably "storage goods" is understood to denote natural substances of vegetable origin and/or their processed forms, more preferably fruits and their processed forms, such as pomes, stone fruits, soft fruits and citrus fruits and their processed forms. In another preferred embodiment of the invention "storage goods" is understood to denote wood.

Therefore a further aspect of the present invention is a method of protecting storage goods, which comprises applying to the storage goods a composition according to the invention.

The composition of the present invention may also be used in the field of protecting technical material against attack of fungi. According to the present invention, the term "technical material" includes paper; carpets; constructions; cooling and heating systems; wall-boards; ventilation and air conditioning systems and the like; preferably "technical material" is understood to denote wall-boards. The composition according the present invention can prevent disadvantageous effects such as decay, discoloration or mold.

The composition according to the invention is generally formulated in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the formulations according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the formulation according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010. The formulations generally comprise from 0.1 to 99% by weight, especially from 0.1 to 95% by weight, of compounds of formula (I) and (II) and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied ata rate of from 1 to 2000 l/ha, especially from 10 to 1000 l/ha.

Certain mixture compositions comprising a compound of formula (I) described above may show a synergistic effect. This occurs whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is:

$$E = X + Y - \frac{X \cdot Y}{100}.$$

If the action actually observed (O) is greater than the expected action (E), then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

However, besides the actual synergistic action with respect to fungicidal activity, the composition according to the invention may also have further surprising advantageous properties. Examples of such advantageous properties that may be mentioned are: more advantageous degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

The composition according to the invention can be applied to the phytopathogenic microorganisms, the useful plants, the locus thereof, the propagation material thereof, storage goods or technical materials threatened by microorganism attack.

The composition according to the invention may be applied before or after infection of the useful plants, the propagation material thereof, storage goods or technical materials by the microorganisms.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is typically applied at a rate of 5 to 2000 g a.i./ha, particularly 10 to 1000 g a.i./ha, e.g. 50, 75, 100 or 200 g a.i./ha, typically in association with 1 to 5000 g a.i./ha, particularly 2 to 2000 g a.i./ha, e.g. 100, 250, 500, 800, 1000, 1500 g a.i./ha of component (B).

In agricultural practice the application rates of the composition according to the invention depend on the type of effect desired, and typically range from 20 to 4000 g of total composition per hectare.

When the composition according to the invention is used for treating seed, rates of 0.001 to 50 g of a compound of component (A) per kg of seed, preferably from 0.01 to 10 g per kg of seed, and 0.001 to 50 g of a compound of component (B), per kg of seed, preferably from 0.01 to 10 g per kg of seed, are generally sufficient.

For the avoidance of doubt, where a literary reference, patent application, or patent, is cited within the text of this application, the entire text of said citation is herein incorporated by reference.

EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Throughout this description, temperatures are given in degrees Celsius and "m.p." means melting point. LC/MS means Liquid Chromatography Mass Spectroscopy and the description of the apparatus and the methods are:

Method G:

Spectra were recorded on a Mass Spectrometer (ACQUITY UPLC) from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+ 0.05% HCOOH, gradient: 10-100% B in 1.2 min; Flow (ml/min) 0.85

Method H:

Spectra were recorded on a Mass Spectrometer (ACQUITY UPLC) from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+ 0.05% HCOOH, gradient: 10-100% B in 2.7 min; Flow (ml/min) 0.85

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

PREPARATION EXAMPLES

Example 1: This Example Illustrates the Preparation of 4,4-difluoro-3,3-dimethyl-1-(8-methylimidazo[1,2-a]pyridin-3-yl)isoquinoline (Compound X.017)

Step 1: 1-(8-bromoimidazo[1,2-a]pyridin-3-yl)-3,3-dimethyl-4H-isoquinoline

To an ice cooled (0° C.) solution of 1.00 g (4.50 mmol) 8-bromoimidazo[1,2-a]pyridine-3-carbonitrile in 9.8 mL conc. sulfuric acid was slowly added 1.01 g (6.76 mmol) 2-methyl-1-phenyl-propan-2-ol over 15 min and the resulting solution was stirred for additional 60 min at 0-5° C. The reaction mixture was poured into ice-water and the pH was adjusted to 9 with 4 N sodium hydroxide solution. The aqueous phase was extracted with ethyl acetate, dried over sodium sulfate, filtrated and concentrated under reduced pressure. The residue was purified by flash chromatography (heptane/ethyl acetate=3:1) to give 1.04 g (2.94 mmol) 1-(8-bromoimidazo[1,2-a]pyridin-3-yl)-3,3-dimethyl-4H-isoquinoline as light yellow powder.

Step 2: 1-(8-bromoimidazo[1,2-a]pyridin-3-yl)-3,3-dimethyl-isoquinolin-4-one

To a solution of 0.625 g (1.77 mmol) 1-(8-bromoimidazo[1,2-a]pyridin-3-yl)-3,3-dimethyl-4H-isoquinoline in 50 mL carbon tetrachloride was added 0.661 g (3.52 mmol) N-bromosuccinimide and 0.076 g (0.44 mmol) azoisobutyronitrile at RT. The resulting mixture was warmed to 77° C. and stirred for 120 min at this temperature. After cooling to RT, the reaction was diluted with dichloromethane, successively washed with water and brine, dried over sodium sulfate, filtrated and concentrated under reduced pressure. The residue was purified by flash chromatography (heptane/ethyl acetate=2:1) to give 0.634 g (1.73 mmol) 1-(8-bromoimidazo[1,2-a]pyridin-3-yl)-3,3-dimethyl-isoquinolin-4-one as off-white solid, m.p. 204-208° C.

Step 3: 1-(8-bromoimidazo[1,2-a]pyridin-3-yl)-4,4-difluoro-3,3-dimethyl-isoquinoline 0.33 g (0.81 mmol) 1-(8-bromoimidazo[1,2-a]pyridin-3-yl)-3,3-dimethyl-isoquinolin-4-one was suspended in 0.51 mL 2,2-difluoro-1,3-dimethylimidazoline at RT, warmed to 100° C. and stirred over night at this temperature. The resulting solution was cooled to RT and slowly added into ice-cold, saturated bicarbonate solution. This mixture was extracted with ethyl acetate; the organic layer was washed with brine, dried over sodium sulfate, filtrated and concentrated under reduced pressure. The residue was purified by flash chromatography (toluene/ethyl acetate=1:0-9:1) to afford 0.136 g (0.35 mmol) 1-(8-bromoimidazo[1,2-a]pyridin-3-yl)-4,4-difluoro-3,3-dimethyl-isoquinoline as white solid, m.p. 173° C.

Step 4: 4,4-difluoro-3,3-dimethyl-1-(8-methylimidazo[1,2-a]pyridin-3-yl)isoquinoline To a solution of 0.09 g (0.23 mmol) 1-(8-bromoimidazo[1,2-a]pyridin-3-yl)-4,4-difluoro-3,3-dimethyl-isoquinoline in 3 mL dioxane (degased) was added 0.072 mL (0.25 mmol) trimethylboroxine (3.5 M in THF), 0.307 g (0.92 mmol) cesium carbonate and 0.020 g (0.02 mmol) [Pd(dppf)Cl2] at RT. The resulting suspension was warmed to 95° C. and maintained for 90 min at this temperature. After cooling to RT, the reaction was diluted with water and extracted with ethyl acetate. The organic layer was washed with brine, dried over sodium sulfate, filtrated and concentrated under reduced pressure. The residue was purified by flash chromatography (heptane/ethyl acetate=3:2-2:1) to afford 0.073 g (0.22 mmol) 4,4-difluoro-3,3-dimethyl-1-(8-methylimidazo[1,2-a]pyridin-3-yl)isoquinoline as light brown oil.

Example 2: This Example Illustrates the Preparation of 1-(6,7-dimethylpyrazolo[1,5-a]pyridin-3-yl)-4,4-difluoro-3,3-dimethyl-isoquinoline (Compound X.011)

Step 1: Preparation of 3,3-dimethyl-2H-isoquinoline-1,4-dione

1) To a solution of 3,3-dimethyl-2,4-dihydroisoquinolin-1-one (57.1 mmol, 10.0 g) in CCl4 (285 mL) at room temperature was added N-bromosuccinimide (171 mmol, 30.5 g) and AIBN (8.5 mmol, 1.43 g) and the reaction mixture was stirred at 70° C. for 3 hours. The reaction mixture was allowed to cool down to room temperature, concentrated under vacuo and diluted with EtOAc, washed with water and brine, dried over Na2SO4, filtered and concentrated to give 4,4-dibromo-3,3-dimethyl-2H-isoquinolin-1-one (25.2 g) as a light yellow solid which was used directly in the next step without further purification: LC-MS (Method H) UV Detection: 220 nm, Rt=1.34; MS: (M+1)=332-334-336; $^1$H NMR (400 MHz, CHLOROFORM-d) δ ppm 1.57 (s, 6H) 7.21 (br. s, 1H) 7.70-7.77 (m, 1H) 7.78-7.85 (m, 1H) 8.06-8.14 (m, 1H) 8.23-8.30 (m, 1H).

2) To a solution of 4,4-dibromo-3,3-dimethyl-2H-isoquinolin-1-one (20.0 g) in a mixture of water (450 mL) and tetrahydrofuran (225 mL) was added sodium carbonate (135 mmol, 14.3 g) and the mixture was stirred at room temperature for 12 h and at 70° C. for 4 h 30 min. The reaction mixture was allowed to cool down to room temperature, diluted with water, acidified to pH 3-4 with 90 mL of a 2 M solution of hydrochloric acid and extracted with dichloromethane. The combined organic extracts were dried over Na2SO4, filtered and concentrated to give 3,3-dimethyl-2H-isoquinoline-1,4-dione (9.95 g) as a yellow solid: LC-MS (Method H) UV Detection: 220 nm, Rt=0.81; MS: (M+1)=190; $^1$H NMR (400 MHz, CHLOROFORM-d) δ ppm 1.77 (s, 3H) 1.97 (s, 3H) 7.39 (s, 1H) 7.46-7.58 (m, 1H) 7.60-7.71 (m, 1H) 7.98-8.22 (m, 2H).

Step 2: Preparation of 1-chloro-3,3-dimethyl-isoquinolin-4-one

To a solution of N,N-dimethylformamide (2.3 mL, 30 mmol) in dichloromethane (52 mL) at room temperature was added oxalyl chloride (20 mmol, 1.8 mL) dropwise over a period of 35 min and the white suspension was vigorously stirred for 15 min until the gas evolution stopped. A solution of 3,3-dimethyl-2H-isoquinoline-1,4-dione (2.5 g, 13 mmol) in dichloromethane (25 mL) was then added dropwise and the mixture was stirred at room temperature for 1 h. The reaction mixture was poured into an ice-cooled mixture of saturated aqueous NaHCO3 solution and pentane, and the organic phase was separated. The aqueous phase was then extracted with pentane, and the combined organic phases were washed with brine, dried over Na2SO4, filtered and concentrated to give 1-chloro-3,3-dimethyl-isoquinolin-4-one (2.5 g) as a yellow solid: LC-MS (Method H) UV Detection: 220 nm, Rt=1.34; MS: (M+1)=208-210; $^1$H NMR (400 MHz, CHLOROFORM-d) δ ppm 1.47 (s, 6H) 7.62-7.69 (m, 1H) 7.73-7.81 (m, 1H) 7.90 (dd, J=8.07, 0.73 Hz, 1H) 8.04 (dd, J=7.50, 0.90 Hz, 1H).

Step 3: Preparation of 3,3-dimethyl-1-(2-trimethylsilylethynyl)isoquinolin-4-one To a solution of 1-chloro-3,3-dimethyl-isoquinolin-4-one (2.10 g, 9.1 mmol) in triethylamine (20 mL) was added at room temperature CuI (0.17 g, 0.9 mmol), bis-triphenylphosphine Palladium(11) dichloride (320 mg, 0.46 mmol) followed by dropwise addition of ethynyltrimethylsilane (1.9 mL, 14 mmol). The black solution was stirred at room temperature for 1 hour. The reaction mixture was quenched with saturated aqueous NH4Cl and the extracted twice with ethyl acetate. The organic phase was washed with brine, dried over anhydrous Na2SO4, filtered and concentrated. Purification by flash chromatography gave 3,3-dimethyl-1-(2-trimethylsilylethynyl)isoquinolin-4-one (2.35 g) as a dark yellow oil: LC-MS (Method G), Rt=1.21 UV Detection: 220 nm; MS: (M+1)=270; $^1$H NMR (400 MHz, CHLOROFORM-d) δ ppm 0.32 (s, 9H) 1.51 (s, 6H) 7.63-7.69 (m, 1H) 7.79-7.83 (m, 1H) 7.98 (dd, 2H) 8.05 (dd, 1H).

Step 4: Preparation of 1-ethynyl-3,3-dimethyl-isoquinolin-4-one

To a solution of 3,3-dimethyl-1-(2-trimethylsilylethynyl)isoquinolin-4-one (1.0 g, 3.7 mmol) in methanol (7.5 mL) was added at room temperature K2CO3 (570 mg, 4.1 mmol). The reaction mixture was stirred at room temperature for 1 h, quenched with water (pH 8/9), and extracted twice with ethyl acetate. The combined organic phases were washed with brine, dried over anhydrous Na2SO4, filtered and concentrated. Purification by flash chromatography gave 1-ethynyl-3,3-dimethyl-isoquinolin-4-one (700 mg) as a brown oil: LC-MS (Method G), Rt=0.84, UV Detection: 220 nm; MS: (M+1)=198; $^1$H NMR (400 MHz, CHLOROFORM-d) δ ppm 1.50 (s, 6H) 3.28 (s, 1H) 7.65-7.70 (m, 1H) 7.79-7.85 (m, 1H) 7.98-8.04 (m, 1H) 8.06-8.12 (s, 1H).

Step 5: Preparation of 1-(6,7-dimethylpyrazolo[1,5-a]pyridin-3-yl)-3,3-dimethyl-isoquinolin-4-one To a white suspension of 2,3-dimethylpyridin-1-ium-1-amine iodide (1.0 g, 4.1 mmol) in dichloromethane (20 mL) was added diazabicycleundecene (623 mg, 4.1 mmol) followed by dropwise addition of 1-ethynyl-3,3-dimethyl-isoquinolin-4-one (700 mg, 3.2 mmol) dissolved in dichloromethane (10 mL), over a period of 30 min. The resulting brown mixture was stirred at room temperature for 1 hour, till disappearance of the 1-ethynyl-3,3-dimethyl-isoquinolin-4-one starting material. The reaction mixture was quenched with water, the organic phase was separated and washed with saturated aqueus $NH_4C_1$. The water phase was extracted with dichloromethane. The combined organic phases were washed with water and brine, dried over anhydrous $Na_2SO_4$, filtered and concentrated. Purification by flash chromatography gave 1-(6,7-dimethylpyrazolo[1,5-a]pyridin-3-yl)-3,3-dimethyl-isoquinolin-4-one (410 mg) as orange solid: mp=152°-153° C., LC-MS (Method G), Rt=0.86, UV Detection: 220 nm; MS: (M+1)=318; $^1$H NMR (400 MHz, CHLOROFORM-d) δ ppm 1.57 (s, 6H) 2.42 (s, 3H) 2.72 (s, 3H) 7.15 (d, 1H) 7.62-7.85 (m, 3H) 8.15 (d, 1H) 8.35 (s, 1H).

Step 6: Preparation of 1-(6,7-dimethylpyrazolo[1,5-a]pyridin-3-yl)-4,4-difluoro-3,3-dimethyl-isoquinoline A solution of 1-(6,7-dimethylpyrazolo[1,5-a]pyridin-3-yl)-3,3-dimethyl-isoquinolin-4-one (370 mg, 1.2 mmol) in 2,2-difluoro-1,3-dimethylimidazolidine (14 mmol, 1.8 ml) was stirred at 105° C. for 24 hours. The reaction mixture was allowed to cool down to room temperature, diluted with dichloromethane then quenched by slow addition to an ice cooled saturated aqueous $NaHCO_3$ solution. The 2 phases were separated, and the aqueous phase was extracted with DCM. The combined organic phases were washed with brine, dried over $Na_2SO_4$, filtered and concentrated. The residue was purified by flash chromatography to give 1-(6,7-dimethylpyrazolo[1,5-a]pyridin-3-yl)-4,4-difluoro-3,3-dimethyl-isoquinoline (328 mg) as a beige solid: mp=160-161° C., LC-MS (Method G) UV Detection: 220 nm, Rt=1.03, MS: (M+1)=340; $^1$H NMR (400 MHz, CHLOROFORM-d) δ ppm 1.42 (s, 6H) 2.40 (s, 3H) 2.79 (s, 3H) 7.15 (d, 1H) 7.57-7.68 (m, 2H) 7.72 (d, 1H) 7.85 (d, 1H) 7.94 (d, 1H) 8.21 (s, 1H). $^{19}$F NMR (400 MHz, CHLOROFORM-d) δ ppm-112.

Alternatively, the compound relating to example 2 can also be prepared by the sequence detailed below:

Step 1: Preparation of 4,4-difluoro-3,3-dimethyl-2H-isoquinolin-1-one

1) To a solution of 3,3-dimethyl-2,4-dihydroisoquinolin-1-one (57.1 mmol, 10.0 g) in CCl4 (285 mL) at room temperature was added N-bromosuccinimide (171 mmol, 30.5 g) and AIBN (8.5 mmol, 1.43 g) and the reaction mixture was stirred at 70° C. for 3 hours. The reaction mixture was allowed to cool down to room temperature, concentrated under vacuo and diluted with EtOAc, washed with water and brine, dried over $Na_2SO_4$, filtered and concentrated to give 4,4-dibromo-3,3-dimethyl-2H-isoquinolin-1-one (25.2 g) as a light yellow solid which was used directly in the next step without further purification: $^1$H NMR (400 MHz, CDCl$_3$) δ ppm 1.57 (s, 6H) 7.21 (br. s, 1H) 7.70-7.77 (m, 1H) 7.78-7.85 (m, 1H) 8.06-8.14 (m, 1H) 8.23-8.30 (m, 1H).

2) To a solution of 4,4-dibromo-3,3-dimethyl-2H-isoquinolin-1-one (7.5 g, 23 mmol) in acetonitrile (11 mL) was added (HF)$_3$-triethylamine (18 g, 110 mmol) at room temperature and the resulting mixture was warmed to 80° C. After stirring for 11 h at 80° C. the reaction was cooled to room temperature and carefully poured into aqueous sodium hydroxide (2 M). The mixture was extracted with ethyl acetate, the organic layer was washed with water, brine, dried over $Na_2SO_4$, filtrated and concentrated in vacuo. The resulting residue was purified by flash chromatography on silica gel to afford the title compound as white solid. LC-MS (Method H) UV Detection: 220 nm, Rt=0.83; MS: (M+1)=212; $^1$H NMR (400 MHz, CDCl$_3$) δ ppm 8.13 (d, 1H), 7.59-7.79 (m, 3H), 6.49 (br. s., 1H), 1.44 (s, 6H).

Step 2: Preparation of 1-chloro-4,4-difluoro-3,3-dimethyl-isoquinoline

To a solution of N,N-dimethylformamide (2.25 mL, 29 mmol) in dichloromethane (27 mL) at 5° C. was added oxalyl chloride (19.3 mmol, 1.72 mL) dropwise over a period of 15 min and the white suspension was vigorously stirred until the gas evolution stopped (ca. 15 min). A solution of 4,4-difluoro-3,3-dimethyl-2H-isoquinolin-1-one (2.69 g, 12.7 mmol) in dichloromethane (18 mL) was then added dropwise, the reaction mixture warmed to room temperature and stirred at this temperature for 1 h. The reaction mixture was poured into an ice-cooled mixture of saturated aqueous $NaHCO_3$ solution and pentane, and the organic phase was separated. The aqueous phase was then extracted with pentane, and the combined organic phases were washed with brine, dried over $Na_2SO_4$, filtered and concentrated to give 1-chloro-4,4-difluoro-3,3-dimethyl-isoquinoline as a yellow solid which was used as such for the next step: LC-MS (Method H) UV Detection: 220 nm, Rt=1.07; MS: (M+1)=230; $^1$H NMR (400 MHz, CDCl$_3$) δ ppm 7.82-7.91 (m, 1H), 7.77 (d, 1H), 7.60-7.71 (m, 2H), 1.39 (s, 6H).

Step 3: Preparation of 2-(4,4-difluoro-3,3-dimethyl-1-isoquinolyl)ethynyl-trimethyl-silane To a solution of 1-chloro-4,4-difluoro-3,3-dimethyl-isoquinoline (2.73 g, 10.7 mmol) in triethylamine (21 mL) was added at room temperature CuI (0.20 g, 1.07 mmol), bis-triphenylphosphine Palladium(11) dichloride (0.19 g, 0.27 mmol) followed by dropwise addition of ethynyltrimethyl-silane (2.2 mL, 16 mmol). The brown solution was stirred at room temperature for 1 hour. The reaction mixture was quenched with saturated aqueous NH$_4$Cl and the extracted twice with ethyl acetate. The organic phase was washed with brine, dried over anhydrous $Na_2SO_4$, filtered and concentrated. Purification by flash chromatography afforded the title compounds as brown oil: LC-MS (Method H), Rt=1.27 UV Detection: 220 nm; MS: (M+1)=292; 1H NMR (400 MHz, CDCl$_3$) δ ppm 7.79-7.91 (m, 1H), 7.68-7.77 (m, 1H), 7.54-7.68 (m, 2H), 1.37 (s, 6H), 0.30 (s, 9H)

Step 4: Preparation of 1-ethynyl-4,4-difluoro-3,3-dimethyl-isoquinoline

To a solution of 2-(4,4-difluoro-3,3-dimethyl-1-isoquinolyl)ethynyl-trimethyl-silane (0.14 g, 0.48 mmol) in isopropanol (2.5 mL) was added at room temperature K$_2$CO$_3$ (0.20 g, 1.44 mmol). The reaction mixture was stirred at room temperature for 3 h, quenched with water (pH 8/9), and extracted twice with ethyl acetate. The combined organic phases were washed with brine, dried over anhydrous Na$_2$SO$_4$, filtered and concentrated. The resulting brown oil was used as such for the next step. LC-MS (Method H), Rt=0.99, UV Detection: 220 nm; MS: (M+1)=220; $^1$H NMR (400 MHz, CDCl$_3$) δ ppm 7.82-7.94 (m, 1H), 7.70-7.81 (m, 1H), 7.54-7.69 (m, 2H), 3.26 (s, 1H), 1.38 (s, 6H).

Step 5: Preparation of 1-(6,7-dimethylpyrazolo[1,5-a]pyridin-3-yl)-4,4-difluoro-3,3-dimethyl-isoquinoline To a white suspension of 2,3-dimethylpyridin-1-ium-1-amine iodide (0.14 g, 0.55 mmol) in dichloromethane (2.5 mL) was added diazabicycloundecene (0.11 g, 0.68 mmol) followed by dropwise addition of 1-ethynyl-4,4-difluoro-3,3-dimethyl-isoquinoline (0.10 g, 0.456 mmol) dissolved in dichloromethane (1.2 mL), over a period of 5 min. The resulting brown mixture was stirred at room temperature for 3 days. The reaction mixture was quenched with water, the organic phase was separated and washed with saturated aqueus NH$_4$Cl. The water phase was extracted with dichloromethane. The combined organic phases were washed with water and brine, dried over anhydrous Na$_2$SO$_4$, filtered and concentrated. Purification by flash chromatography on silica gel afforded the title compounds as light yellow solid. Analytical data was identical with material prepared through the sequence described in example 4.

Example 3: This Example Illustrate the Preparation of 1-(6,7-dimethylpyrazolo[1,5-a]pyridin-3-yl)-4,4,6-trifluoro-3,3-dimethyl-isoquinoline(Compound X.009)

Step 1: Preparation of 6-fluoro-3,3-dimethyl-2H-isoquinoline-1,4-dione

Preparation was performed via an analogous synthetic route to that described for 3,3-dimethyl-2H-isoquinoline-1,4-dione 6-fluoro-3,3-dimethyl-2H-isoquinoline-1,4-dione (example 4, step 1): LC-MS (Method H) UV Detection: 220 nm, Rt=0.94; MS: (M+1)=208; 1H NMR (400 MHz, CHLOROFORM-d) δ ppm 1.56 (s, 6H) 7.35 (br. s, 1H) 7.43-7.50 (m, 1H) 7.68-7.74 (m, 1H) 8.25-8.30 (m, 1H). 19F (400 MHz, CHLOROFORM-d) δ ppm-103

Step 2: Preparation of 1-chloro-6-fluoro-3,3-dimethyl-isoquinolin-4-one

To a solution of N,N-dimethylformamide (1.6 mL, 21 mmol) in dichloromethane (36 mL) at room temperature was added oxalyl chloride (14 mmol, 1.6 mL) dropwise over a period of 30 min and the white suspension was vigorously stirred for 25 min until the gas evolution stopped. A solution of 6-fluoro-3,3-dimethyl-2H-isoquinoline-1,4-dione (2.0 g, 9.7 mmol) in dichloromethane (20 mL) was then added dropwise at 0° C. The mixture was allowed to warm to ambient temperature and stirred for 1 hour. The reaction mixture was poured into an ice-cooled mixture of saturated aqueous NaHCO$_3$ solution and pentane, and the organic phase was separated. The aqueous phase was then extracted with pentane, and the combined organic phases were washed with brine, dried over Na$_2$SO$_4$, filtered and concentrated to give 1-chloro-6-fluoro-3,3-dimethyl-isoquinolin-4-one (1.95 g) as a dark yellow oil, that was used without purification in the next synthetic step: LC-MS (Method H) UV Detection: 220 nm, Rt=1.42; MS: (M+1)=226-228

Step 3: Preparation of 6-fluoro-3,3-dimethyl-1-(2-trimethylsilylethynyl)isoquinolin-4-one To a solution of 1-chloro-6-fluoro-3,3-dimethyl-isoquinolin-4-one (1.4 g, 6.0 mmol) in triethylamine (12 mL) was added at room temperature CuI (116 mg, 0.6 mmol), bis-triphenylphosphine Palladium(11) dichloride (214 mg, 0.3 mmol) followed by dropwise addition of ethynyltrimethylsilane (1.3 mL, 9.1 mmol). The black solution was stirred at room temperature overnight. The reaction mixture was quenched with saturated aqueous NH$_4$C$_1$ and the extracted twice with ethyl acetate. The organic phase was washed with brine, dried over anhydrous Na$_2$SO$_4$, filtered and concentrated. Purification by flash chromatography gave 6-fluoro-3,3-dimethyl-1-(2-trimethylsilylethynyl)isoquinolin-4-one (1.25 g) as a oranfe solid: LC-MS (Method G), Rt=1.22 UV Detection: 220 nm; MS: (M+1)=288; $^1$H NMR (400 MHz, CHLOROFORM-d) δ ppm 0.32 (s, 9H) 1.52 (s, 6H) 7.47-7.52 (m, 1H) 7.70-7.76 (m, 1H) 8.0-8.05 (m, 1H). $^{19}$F (400 MHz, CHLOROFORM-d) δ ppm—104.

Step 4: Preparation of 1-ethynyl-6-fluoro-3,3-dimethyl-isoquinolin-4-one

To a solution of 6-fluoro-3,3-dimethyl-1-(2-trimethylsilylethynyl)isoquinolin-4-one (1.25, 4.3 mmol) in dichloromethane (17 mL) was added at room temperature potassium fluoride (0.56 g, 9.6 mmol) and 18-crown-6 (1.2 g, 4.3 mmol). The reaction mixture was stirred at room temperature for 30 min, quenched with saturated aqueous NaHCO$_3$, and extracted twice with dichloromethane. The combined organic phases were washed with brine, dried over anhydrous Na$_2$SO$_4$, filtered and concentrated. Purification by flash chromatography gave 1-ethynyl-6-fluoro-3,3-dimethyl-isoquinolin-4-one. (610 mg) as a brown oil: LC-MS (Method G), Rt=0.90, UV Detection: 220 nm; MS: (M+1)=216; $^1$H NMR (400 MHz, CHLOROFORM-d) δ ppm 1.53 (s, 6H) 3.31 (s, 1H) 7.46-7.52 (m, 1H) 7.70-7.75 (m, 1H) 8.02-8.07 (m, 1H). $^{19}$F (400 MHz, CHLOROFORM-d) δ ppm-103

Step 5: Preparation of 1-(6,7-dimethylpyrazolo[1,5-a]pyridin-3-yl)-6-fluoro-3,3-dimethyl-isoquinolin-4-one To a solution of 2,3-dimethylpyridin-1-ium-1-amine 2,4,6-trimethylbenzenesulfonate (750 mg, 2.3 mmol) in dimethylformamide (8 mL) was first added potassium carbonate (490 mg, 3.5 mmol) followed by dropwise addition of 1-ethynyl-6-fluoro-3,3-dimethyl-isoquinolin-4-one (600 mg, 2.8 mmol) dissolved in dimethylformamide (4 mL), over a period of 30 min. The resulting brown mixture was stirred at room temperature for 2 days, till disappearance of the 1-ethynyl-5-fluoro-3,3-dimethyl-isoquinolin-4-one starting material. The reaction mixture was quenched with water, and extracted twice with ethyl acetate. The combined organic phases were washed with water and brine, dried over anhydrous Na$_2$SO$_4$, filtered and concentrated. Purification by flash chromatography gave 1-(6,7-dimethylpyrazolo[1,5-a]pyridin-3-yl)-6-fluoro-3,3-dimethyl-isoquinolin-4-one (295 mg) as a brown solid: mp=168-170° C., LC-MS (Method G), Rt=0.92, UV Detection: 220 nm; MS: (M+1)=336; $^1$H NMR (400 MHz, CHLOROFORM-d) δ ppm 1.60 (s, 6H) 2.45 (s, 3H) 2.80 (s, 3H) 7.18 (d, 1H) 7.39-7.48 (m, 1H) 7.73-7.95 (m, 3H) 8.23 (br s, 1H). $^{19}$F NMR (400 MHz, CHLOROFORM-d) δ ppm-106

Step 6: Preparation of 1-(6,7-dimethylpyrazolo[1,5-a]pyridin-3-yl)-4,4,6-trifluoro-3,3-dimethyl-isoquinoline A solution of 1-(6,7-dimethylpyrazolo[1,5-a]pyridin-3-yl)-6-fluoro-3,3-dimethyl-isoquinolin-4-one (280 mg, 0.84 mmol) in 2,2-difluoro-1,3-dimethylimidazolidine (1.3 ml) was stirred at 105° C. for 24 hours. The reaction mixture was allowed to cool down to room temperature, diluted with dichloromethane then quenched by slow addition to an ice cooled saturated aqueous NaHCO$_3$ solution. The two phases were separated, and the aqueous phase was extracted with DCM. The combined organic phases were washed with brine, dried over Na$_2$SO$_4$, filtered and concentrated. The residue was purified by flash chromatography to give 1-(6,7-dimethylpyrazolo[1,5-a]pyridin-3-yl)-4,4,6-trifluoro-3,3-dimethyl-isoquinoline (235 mg) as a beige solid: mp=183-185° C., LC-MS (Method G) UV Detection: 220 nm, Rt=1.09, MS: (M+1)=358; $^1$H NMR (400 MHz, CHLOROFORM-d) δ ppm 1.45 (s, 6H) 2.45 (s, 3H) 2.80 (s, 3H) 7.19 (d, 1H) 7.22-7.27 (m, 1H) 7.55 (dd, 1H) 7.72-7.77 (m, 1H) 7.95 (d, 1H) 8.21 (br s, 1H). $^{19}$F NMR (400 MHz, CHLOROFORM-d) δ ppm-106, -113.

Example 4: This Example Illustrates the 1-(6,7-dimethylpyrazolo[1,5-a]pyridin-3-yl)-4,4,5-trifluoro-3,3-dimethyl-isoquinoline (Compound X.008)

Step 1: Preparation of
5-fluoro-3,3-dimethyl-2H-isoquinoline-1,4-dione

1) To a solution of 5-fluoro-3,3-dimethyl-2,4-dihydroisoquinolin-1-one (5.0 g, 25.9 mmol) in CCl4 (100 mL) at room temperature was added N-bromosuccinimide (44 mmol, 7.9 g) and AIBN (2.6 mmol, 0.43 g) and the reaction mixture was stirred at 70° C. for 2 hours, until starting material has disappeared. The reaction mixture was allowed to cool down to room temperature, concentrated under vacuo and diluted with ethyl acetate, washed with water and brine, dried over Na$_2$SO$_4$, filtered and concentrated to give 4-bromo-5-fluoro-3,3-dimethyl-2,4-dihydroisoquinolin-1-one (6.6 g) as a light yellow solid which was used directly in the next step without further purification: LC-MS (Method G) UV Detection: 220 nm, Rt=0.83; MS: (M+1)=272-274; $^1$H NMR (400 MHz, CHLOROFORM-d) δ ppm 1.30 (s, 3H) 1.55 (s, 3H) 5.30 (s, 1H) 6.15 (br. s, 1H) 7.24-7.30 (m, 1H) 7.40-7.50 (m, 1H) 7.90 (d, 1H). $^{19}$F NMR (400 MHz, CHLOROFORM-d) δ ppm-119

2) A solution of 4-bromo-5-fluoro-3,3-dimethyl-2,4-dihydroisoquinolin-1-one (6.6 g) in a mixture of water (120 mL) and tetrahydrofuran (120 mL) was stirred at 90° C. overnight. The reaction mixture was allowed to cool down to room temperature, diluted with saturated aqueous NaHCO$_3$ to pH 7-8 and extracted with ethyl acetate. The combined organic extracts were dried over Na$_2$SO$_4$, filtered and concentrated. Purification by flash chromatography gave 5-fluoro-4-hydroxy-3,3-dimethyl-2,4-dihydroisoquinolin-1-one (3.54 g) as a white solid: LC-MS (Method G) UV Detection: 220 nm, Rt=0.60; MS: (M+1)=210; $^1$H NMR (400 MHz, CHLOROFORM-d) δ ppm 1.20 (s, 3H) 1.50 (s, 3H) 2.5 (br. d, 1H) 4.7 (d, 1H) 5.75 (br. s, 1H) 7.27-7.30 (m, 1H) 7.40-7.48 (m, 1H) 7.85 (d, 1H). $^{19}$F NMR (400 MHz, CHLOROFORM-d) δ ppm-113

3) To a solution of 5-fluoro-4-hydroxy-3,3-dimethyl-2,4-dihydroisoquinolin-1-one (3.54 g, 16.9 mmol) in dichloromethane (200 ml) was added Dess-Martin periodinane (18.6 mmol, 8.15 g) at 0° C. The reaction mixture was stirred for 2 hour at temperature between 0 and 10° C. and quenched with saturated aqueous NaHCO$_3$. The organic phase was separated and washed with sodium thiosulfate solution and brine, dried over Na$_2$SO$_4$ and concentrated under reduced pressure. The residue was purified by flash chromatography to give 5-fluoro-3,3-dimethyl-2H-isoquinoline-1,4-dione (3.08 g) as a white solid: LC-MS (Method G) UV Detection: 220 nm, Rt=0.68; MS: (M+1)=208; $^1$H NMR (400 MHz, CHLOROFORM-d) δ ppm 1.53 (s, 6H) 2.5 (br. d, 1H) 4.7 (d, 1H) 6.52 (br. s, 1H) 7.38-7.43 (m, 1H) 7.72-7.8 (m, 1H) 8.10 (d, 1H).

Step 2: Preparation of
1-chloro-5-fluoro-3,3-dimethyl-isoquinolin-4-one

To a solution of dimethylformamide (1.0 mL, 13.5 mmol) in dichloromethane (25 mL), at room temperature, was added oxalyl chloride (1.2 mL, 13.5 mmol) dropwise over a period of 30 min the white suspension was vigorously stirred at the same temperature for 1 hour until the gas evolution stopped. A solution of 5-fluoro-3,3-dimethyl-2H-isoquinoline-1,4-dione (2.0 g, 9.65 mmol) in dichloromethane (25 mL) was then added dropwise and the mixture was stirred at room temperature for 1 hour. The reaction mixture was poured into an ice-cooled saturated aqueous NaHCO$_3$ solution and pentane, and the organic phase was separated. The aqueous phase was then extracted with pentane, and the combined organic phases were washed with brine, dried over Na$_2$SO$_4$, filtered and concentrated to give 1-chloro-5-fluoro-3,3-dimethyl-isoquinolin-4-one (2.05 g) as a yellow solid: LC-MS (Method G), Rt=0.91 UV Detection: 220 nm; MS: (M+1)=226-228; $^1$H NMR (400 MHz, CHLOROFORM-d) δ ppm 1.52 (s, 6H) 7.36-7.44 (m, 1H) 7.77-7.81 (m, 2H).

Step 3: Preparation of 5-fluoro-3,3-dimethyl-1-(2-trimethylsilylethynyl)isoquinolin-4-one To a solution of 1-chloro-5-fluoro-3,3-dimethyl-isoquinolin-4-one (2.04 g, 9.0 mmol) in triethylamine (18 mL) was added at room temperature CuI (174 mg, 0.90 mmol), bis-triphenylphosphine Palladium(11) dichloride (0.32 g, 0.45 mmol) followed by dropwise addition of ethynyltrimethylsilane (1.9 mL, 13.6 mmol). The black solution was stirred at room temperature for 1 hour. The reaction mixture was quenched with saturated aqueous NH$_4$Cl and the extracted twice with ethyl acetate. The organic phase was washed with brine, dried over anhydrous Na$_2$SO$_4$, filtered and concentrated. Purification by flash chromatography gave 5-fluoro-3,3-dimethyl-1-(2-trimethylsilylethynyl)isoquinolin-4-one (2.25 g) as a yellow solid: LC-MS (Method G), Rt=1.16 UV Detection: 220 nm; MS: (M+1)=288; $^1$H NMR (400 MHz, CHLOROFORM-d) δ ppm 0.30 (s, 9H) 1.51 (s, 6H) 7.29-7.34 (m, 1H) 7.75-7.81 (m, 2H). $^{19}$F (400 MHz, CHLOROFORM-d) δ ppm—108.

Step 4: Preparation of
1-ethynyl-5-fluoro-3,3-dimethyl-isoquinolin-4-one

To a solution of 5-fluoro-3,3-dimethyl-1-(2-trimethylsilylethynyl)isoquinolin-4-one (2.25 g, 7.8 mmol) in dichloromethane (31 mL) was added at room temperature potassium fluoride (2.2 eq, 1.0 g, 17.2 mmol) and 18-crown-6 (2.09 g, 7.8 mmol). The reaction mixture was stirred at room temperature for 30 min, quenched with saturated aqueous NaHCO$_3$, and extracted twice with dichloromethane. The combined organic phases were washed with brine, dried over anhydrous Na$_2$SO$_4$, filtered and concentrated. Purification by flash chromatography gave 1-ethynyl-5-fluoro-3,3-dimethyl-isoquinolin-4-one (1.46 g) as a yellow solid: LC-MS (Method G), Rt=0.83, UV Detection: 220 nm; MS:

(M+1)=216; ¹H NMR (400 MHz, CHLOROFORM-d) δ ppm 1.50 (s, 6H) 3.28 (s, 1H) 7.32-7.37 (m, 1H) 7.75-7.83 (m, 2H).

Step 5: Preparation of 1-(6,7-dimethylpyrazolo[1,5-a]pyridin-3-yl)-5-fluoro-3,3-dimethyl-isoquinolin-4-one To a solution of 2,3-dimethylpyridin-1-ium-1-amine 2,4,6-trimethylbenzenesulfonate (1.0 g, 3.1 mmol) in dimethylformamide (16 mL) was first added potassium carbonate (650 mg, 4.6 mmol) followed by dropwise addition of 1-ethynyl-5-fluoro-3,3-dimethyl-isoquinolin-4-one (1.0 g, 4.65 mmol) dissolved in dimethylformamide (6 mL), over a period of 30 min. The resulting brown mixture was stirred at room temperature for 16 hours, till disappearance of the 1-ethynyl-5-fluoro-3,3-dimethyl-isoquinolin-4-one starting material. The reaction mixture was quenched with water, and extracted twice with ethyl acetate. The combined organic phases were washed with water and brine, dried over anhydrous $Na_2SO_4$, filtered and concentrated. Purification by flash chromatography gave 1-(6,7-dimethylpyrazolo[1,5-a]pyridin-3-yl)-5-fluoro-3,3-dimethyl-Isoquinolin-4-one (380 mg) as a brown solid: mp=139-141° C., LC-MS (Method G), Rt=0.95, UV Detection: 220 nm; MS: (M+1)=336; ¹H NMR (400 MHz, CHLOROFORM-d) δ ppm 1.54 (s, 6H) 2.38 (s, 3H) 2.75 (s, 3H) 7.15 (d, 1H) 7.32 (t, 1H) 7.58 (d, 1H) 7.68-7.71 (m, 1H) 7.78 (d, 1H) 8.16 (s, 1H). ¹⁹F NMR (400 MHz, CHLOROFORM-d) δ ppm—112.

Step 6: Preparation of 1-(6,7-dimethylpyrazolo[1,5-a]pyridin-3-yl)-4,4,5-trifluoro-3,3-dimethyl-isoquinoline A solution of 1-(6,7-dimethylpyrazolo[1,5-a]pyridin-3-yl)-5-fluoro-3,3-dimethyl-isoquinolin-4-one (360 mg, 1.1 mmol) in 2,2-difluoro-1,3-dimethylimidazolidine (1.7 ml) was stirred at 105° C. for 24 hours. The reaction mixture was allowed to cool down to room temperature, diluted with dichloromethane then quenched by slow addition to an ice cooled saturated aqueous $NaHCO_3$ solution. The two phases were separated, and the aqueous phase was extracted with DCM. The combined organic phases were washed with brine, dried over $Na_2SO_4$, filtered and concentrated. The residue was purified by flash chromatography to give 1-(6,7-dimethylpyrazolo[1,5-a]pyridin-3-yl)-4,4,5-trifluoro-3,3-dimethyl-isoquinoline (310 mg) as a beige solid: mp=185-187° C., LC-MS (Method G) UV Detection: 220 nm, Rt=1.14, MS: (M+1)=358; ¹H NMR (400 MHz, CHLOROFORM-d) δ ppm 1.45 (s, 6H) 2.40 (s, 3H) 2.78 (s, 3H) 7.17 (d, 1H) 7.31 (t, 1H) 7.51-7.60 (m, 2H) 7.90 (d, 1H) 8.15 (s, 1H). ¹⁹F NMR (400 MHz, CHLOROFORM-d) δ ppm—110, -113.

The following table gives analytical data for compounds of formula (I) prepared using synthetic techniques described above.

TABLE E

Physical data of compounds of formula (I) as represented in Table X (above).

| No. | Compound name | STRUCTURE | RT (min) | [M + H] (measured) | Method | MP (° C.) |
|---|---|---|---|---|---|---|
| X.001 | 1-(6-chloro-7-methyl-pyrazolo[1,5-a]pyridin-3-yl)-4,4-difluoro-3,3-dimethyl-isoquinoline | 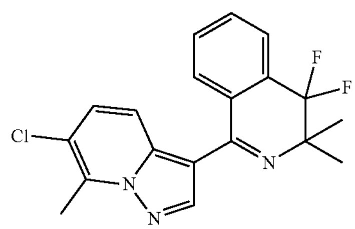 [SMILES: Cc1c(Cl)ccc2c(C3=NC(C)(C)C(F)(F)c4ccccc43)cnn12] | 1.23 | 360-362 | G | 166-168 |
| X.002 | 4,4-difluoro-1-(6-fluoro-7-methyl-pyrazolo[1,5-a]pyridin-3-yl)-3,3-dimethyl-isoquinoline | 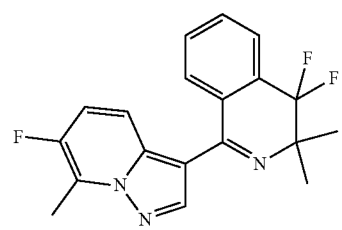 [SMILES: Cc1c(F)ccc2c(C3=NC(C)(C)C(F)(F)c4ccccc43)cnn12] | 1.13 | 344 | G | 115-118 |
| X.003 | 1-(6-chloropyrazolo[1,5-a]pyridin-3-yl)-4,4-difluoro-3,3-dimethyl-isoquinoline | 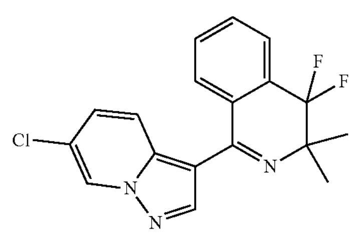 [SMILES: CC1(C)N=C(c2cnn3cc(Cl)ccc23)c2ccccc2C1(F)F] | 1.16 | 346-348 | G | 113-118 |

TABLE E-continued

Physical data of compounds of formula (I) as represented in Table X (above).

| No. | Compound name | STRUCTURE | RT (min) | [M + H] (measured) | Method | MP (° C.) |
|---|---|---|---|---|---|---|
| X.004 | 1-(6-ethylpyrazolo[1,5-a]pyridin-3-yl)-4,4-difluoro-3,3-dimethyl-isoquinoline | 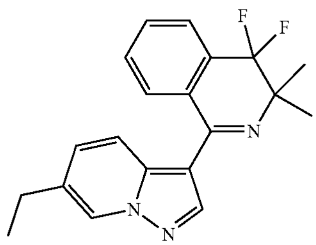 [SMILES: CCc1ccc2c(C3=NC(C)(C)C(F)(F)c4ccccc43)cnn2c1] | 1.04 | 340 | G | |
| X.005 | 4,4-difluoro-3,3-dimethyl-1-(6-methylpyrazolo[1,5-a]pyridin-3-yl)isoquinoline | 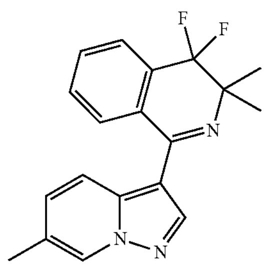 | 0.96 | 326 | G | 105-107 |
| X.006 | 1-(6-bromopyrazolo[1,5-a]pyridin-3-yl)-4,4-difluoro-3,3-dimethyl-isoquinoline | 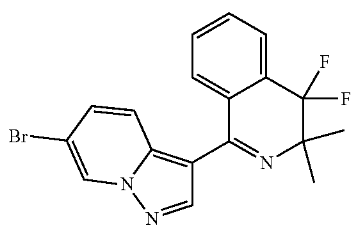 [SMILES: CC1(C)N=C(c2cnn3cc(Br)ccc23)c2ccccc2C1(F)F] | 1.17 | 390-392 | G | 127-129 |
| X.007 | 1-(6-bromo-7-methyl-pyrazolo[1,5-a]pyridin-3-yl)-4,4-difluoro-3,3-dimethyl-isoquinoline | 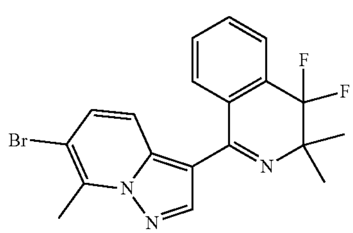 [SMILES: Cc1c(Br)ccc2c(C3=NC(C)(C)C(F)(F)c4ccccc43)cnn12] | 1.34 | 404-406 | G | 180-182 |
| X.008 | 1-(6,7-dimethylpyrazolo[1,5-a]pyridin-3-yl)-4,4,5-trifluoro-3,3-dimethyl-isoquinoline | 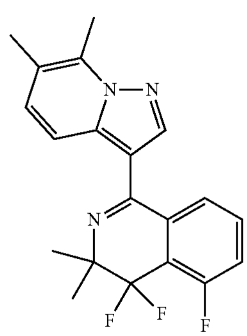 [SMILES: Cc1ccc2c(C3=NC(C)(C)C(F)(F)c4c(F)cccc43)cnn2c1C] | 1.14 | 358 | G | 185-187 |

TABLE E-continued

Physical data of compounds of formula (I) as represented in Table X (above).

| No. | Compound name | STRUCTURE | RT (min) | [M + H] (measured) | Method | MP (° C.) |
| --- | --- | --- | --- | --- | --- | --- |
| X.009 | 1-(6,7-dimethylpyrazolo[1,5-a]pyridin-3-yl)-4,4,6-trifluoro-3,3-dimethyl-isoquinoline | 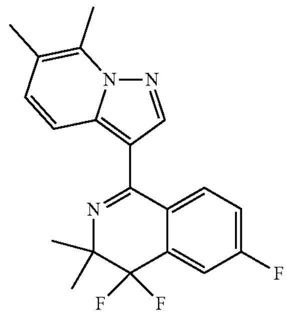 [SMILES: Cc1ccc2c(C3=NC(C)(C)C(F)(F)c4cc(F)ccc43)cnn2c1C] | 1.09 | 358 | G | 183-185 |
| X.010 | 4,4-difluoro-3,3-dimethyl-1-(7-methylpyrazolo[1,5-a]pyridin-3-yl)isoquinoline | 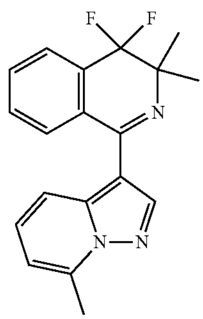 [SMILES: Cc1cccc2c(C3=NC(C)(C)C(F)(F)c4ccccc43)cnn12] | 0.97 | 326 | G | 105-107 |
| X.011 | 1-(6,7-dimethylpyrazolo[1,5-a]pyridin-3-yl)-4,4-difluoro-3,3-dimethyl-isoquinoline | 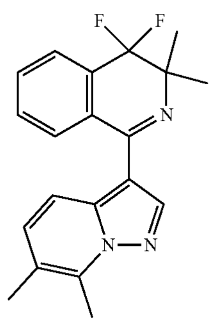 | 1.03 | 340 | G | 160-161 |
| X.012 | 1-(6,7-dimethylpyrazolo[1,5-a]pyridin-3-yl)-5-fluoro-3,3,4,4-tetramethyl-isoquinoline | 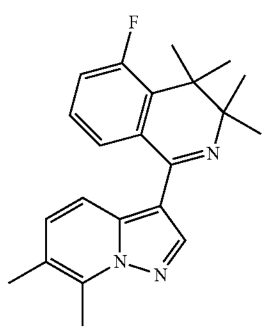 | 0.88 | 350 | G | 175-176 |
| X.013 | 5-fluoro-3,3,4,4-tetramethyl-1-(7-methylpyrazolo[1,5-a]pyridin-3-yl)isoquinoline | 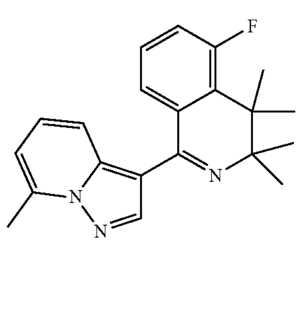 | 0.81 | 336 | G | 134-136 |

TABLE E-continued

Physical data of compounds of formula (I) as represented in Table X (above).

| No. | Compound name | STRUCTURE | RT (min) | [M + H] (measured) | Method | MP (° C.) |
|---|---|---|---|---|---|---|
| X.014 | 1-(7,8-dimethylimidazo[1,2-a]pyridin-3-yl)-4,4-difluoro-3,3-dimethyl-isoquinoline | 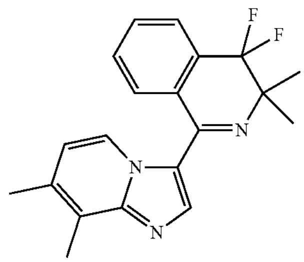 | 0.88 | 340 | G | 159-161 |
| X.015 | 4,4-difluoro-3,3-dimethyl-1-(7-methylimidazo[1,2-a]pyridin-3-yl)isoquinoline | 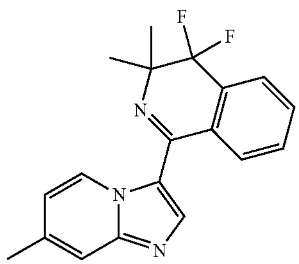 [SMILES: Cc1ccn2c(C3=NC(C)(C)C(F)(F)c4ccccc43)cnc2c1] | 1.26 | 326.3 | H | |
| X.016 | 1-(7,8-dimethylimidazo[1,2-a]pyridin-3-yl)-5-fluoro-3,3,4,4-tetramethyl-isoquinoline | 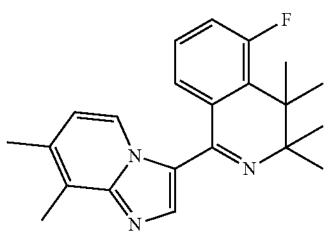 | 0.91 | 350 | G | 185-186 |
| X.017 | 4,4-difluoro-3,3-dimethyl-1-(8-methylimidazo[1,2-a]pyridin-3-yl)isoquinoline | 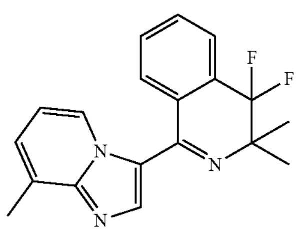 [SMILES: Cc1cccn2c(C3=NC(C)(C)C(F)(F)c4ccccc43)cnc12] | 0.95 | 326 | G | |
| X.018 | 5-fluoro-3,3,4,4-tetramethyl-1-(7-methylimidazo[1,2-a]pyridin-3-yl)isoquinoline | 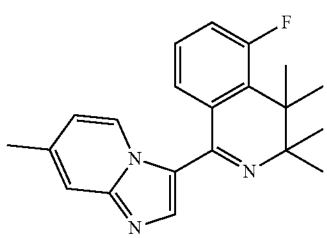 | 1.02 | 336 | G | |
| X.019 | 5-fluoro-3,3,4,4-tetramethyl-1-(8-methylimidazo[1,2-a]pyridin-3-yl)isoquinoline | 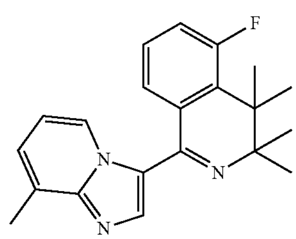 | 0.95 | 336 | G | 160-161 |

BIOLOGICAL EXAMPLES

Example A1: *Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Botryotinia fuckeliana* at 20 ppm when compared to untreated control under the same conditions, which showed extensive disease development:

X.001, X.002, X.003, X.004, X.005, X.006, X.007, X.008, X.009, X.010, X.011, X.012, X.013, X.014, X.015, X.016, X.017, X.018, X.019.

Example A2: *Glomerella lagenarium* (*Colletotrichum lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds gave at least 80% control of *Glomerella* lagenarium at 20 ppm when compared to untreated control under the same conditions, which showed extensive disease development:

X.001, X.002, X.003, X.004, X.005, X.006, X.007, X.008, X.009, X.010, X.011, X.012, X.013, X.014, X.015, X.016, X.017, X.018, X.019.

Example A3: *Fusarium culmorum*/Liquid Culture (Head Blight)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Fusarium culmorum* at 20 ppm when compared to untreated control under the same conditions, which showed extensive disease development:

X.001, X.002, X.003, X.004, X.005, X.006, X.007, X.008, X.009, X.010, X.011, X.012, X.013, X.014, X.015, X.016, X.017, X.018, X.019.

Example A4: *Gaeumannomyces graminis*/Liquid Culture (Take-all of Cereals)

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores iss added. The test plates are incubated at 24° C. and the inhibition of growth is determined photometrically 4-5 days after application. The following compounds gave at least 80% control of *Gaeumannomyces graminis* at 20 ppm when compared to untreated control under the same conditions, which showed extensive disease development:

X.001, X.002, X.003, X.004, X.005, X.006, X.007, X.008, X.010, X.011, X.012, X.019.

Example A5: *Monographella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Monographella nivalis* at 20 ppm when compared to untreated control under the same conditions, which showed extensive disease development:

X.001, X.002, X.005, X.006, X.008, X.009, X.010, X.011, X.013, X.014, X.017, X.019.

Example A6: *Mycosphaerella graminicola* (*Septoria tritici*)/Liquid Culture (*Septoria* Blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Mycosphaerella graminicola* at 20 ppm when compared to untreated control under the same conditions, which showed extensive disease development:

X.002, X.003, X.004, X.005, X.006.

Example A7: *Magnaporthe grisea* (*Pyricularia oryzae*)/Rice/Leaf Disc Preventative (Rice Blast)

Rice leaf segments cv. Ballila are placed on agar in a multiwell plate (24-well format) and sprayed with the formulated test compound diluted in water. The leaf segments are inoculated with a spore suspension of the fungus 2 days after application. The inoculated leaf segments are incubated at 22° C. and 80% r.h. under a light regime of 24 h darkness followed by 12 h light/12 h darkness in a climate cabinet and the activity of a compound is assessed as percent disease control compared to untreated when an appropriate level of disease damage appears in untreated check leaf segments (5-7 days after application).

The following compounds gave at least 50% control of *Magnaporthe grisea* at 200 ppm when compared to untreated control under the same conditions, which showed extensive disease development:

X.001, X.002, X.003, X.004, X.005, X.006, X.008, X.009, X.012, X.013, X.017, X.018, X.019.

Example A8: *Magnaporthe grisea* (*Pyricularia oryzae*)/Liquid Culture (Rice Blast)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application. The following compounds gave at least 80% control of *Magnaporthe grisea* at 60 ppm when compared to untreated control under the same conditions, which showed extensive disease development:

X.001, X.002, X.003, X.004, X.005, X.006, X.007, X.008, X.009, X.010, X.011, X.012, X.014, X.015, X.016.

Example A9: *Sclerotinia sclerotiorum*/Liquid Culture (Cottony Rot)

Mycelia fragments of a newly grown liquid culture of the fungus are directly mixed into nutrient broth (Vogels broth). After placing a (DMSO) solution of test compound into a microtiter plate (96-well format) the nutrient broth containing the fungal material is added. The test plates are incubated at 24° C. and the inhibition of growth is determined photometrically 3-4 days after application. The following compounds gave at least 80% control of *Sclerotinia sclerotiorum* at 20 ppm when compared to untreated control under the same conditions, which showed extensive disease development:

X.001, X.002, X.003, X.004, X.005, X.006, X.007, X.008, X.009, X.010, X.011, X.014, X.015, X.016.

Further Biolgical Test Examples

Example B1: *Botrytis cinerea* (Gray Mould)

Conidia of the fungus from cryogenic storage were directly mixed into nutrient broth (PDB potato dextrose broth). A DMSO solution of the test compounds was placed into a microtiter plate (96-well format) and the nutrient broth containing the fungal spores was added to it. The test plates were incubated at 24° C. and the inhibition of growth was determined photometrically after 72 hrs.

The following mixture compositions (A:B) at the reported concentration (in ppm) gave at least 80% disease control in this test.

| Component A | Component B | Ratio A:B | Conc. (ppm) (A:B) |
|---|---|---|---|
| Compound X.011 | pydiflumetofen | 1:2.5 | 0.08:0.2 |
| Compound X.011 | pydiflumetofen | 1:5 | 0.04:0.2 |
| Compound X.011 | pydiflumetofen | 1:10 | 0.02:0.2 |
| Compound X.011 | pydiflumetofen | 1:20 | 0.02:0.4 |
| Compound X.011 | pydiflumetofen | 1:40 | 0.02:0.8 |
| Compound X.011 | azoxystrobin | 1:2.5 | 0.08:0.2 |
| Compound X.011 | azoxystrobin | 1:5 | 0.04:0.2 |
| Compound X.011 | azoxystrobin | 1:10 | 0.02:0.2 |
| Compound X.011 | azoxystrobin | 1:20 | 0.02:0.4 |
| Compound X.011 | azoxystrobin | 1:40 | 0.02:0.8 |
| Compound X.011 | chlorothalonil | 1:25 | 0.08:2 |
| Compound X.011 | chlorothalonil | 1:50 | 0.04:2 |
| Compound X.011 | chlorothalonil | 1:100 | 0.02:2 |
| Compound X.011 | chlorothalonil | 1:200 | 0.02:4 |
| Compound X.011 | chlorothalonil | 1:400 | 0.02:8 |
| Compound X.011 | cyprodinil | 1:2.5 | 0.08:0.2 |
| Compound X.011 | cyprodinil | 1:5 | 0.04:0.2 |
| Compound X.011 | cyprodinil | 1:10 | 0.02:0.2 |
| Compound X.011 | cyprodinil | 1:20 | 0.02:0.4 |
| Compound X.011 | cyprodinil | 1:40 | 0.02:0.8 |
| Compound X.011 | difenoconazole | 1:25 | 0.08:2 |
| Compound X.011 | difenoconazole | 1:50 | 0.04:2 |
| Compound X.011 | difenoconazole | 1:100 | 0.02:2 |
| Compound X.011 | difenoconazole | 1:200 | 0.02:4 |

-continued

| Component A | Component B | Ratio A:B | Conc. (ppm) (A:B) |
|---|---|---|---|
| Compound X.011 | difenoconazole | 1:400 | 0.02:8 |
| Compound X.011 | fluazinam | 1:2.5 | 0.08:0.2 |
| Compound X.011 | fluazinam | 1:5 | 0.04:0.2 |
| Compound X.011 | fluazinam | 1:10 | 0.02:0.2 |
| Compound X.011 | fluazinam | 1:20 | 0.02:0.4 |
| Compound X.011 | fluazinam | 1:40 | 0.02:0.8 |
| Compound X.011 | fludioxonil | 1:2.5 | 0.08:0.2 |
| Compound X.011 | fludioxonil | 1:5 | 0.04:0.2 |
| Compound X.011 | fludioxonil | 1:10 | 0.02:0.2 |
| Compound X.011 | fludioxonil | 1:20 | 0.02:0.4 |
| Compound X.011 | fludioxonil | 1:40 | 0.02:0.8 |
| Compound X.011 | isopyrazam | 1:25 | 0.08:2 |
| Compound X.011 | isopyrazam | 1:50 | 0.04:2 |
| Compound X.011 | isopyrazam | 1:100 | 0.02:2 |
| Compound X.011 | isopyrazam | 1:200 | 0.02:4 |
| Compound X.011 | isopyrazam | 1:400 | 0.02:8 |
| Compound X.011 | benzovindiflupyr | 1:2.5 | 0.08:0.2 |
| Compound X.011 | benzovindiflupyr | 1:5 | 0.04:0.2 |
| Compound X.011 | benzovindiflupyr | 1:10 | 0.02:0.2 |
| Compound X.011 | benzovindiflupyr | 1:20 | 0.02:0.4 |
| Compound X.011 | benzovindiflupyr | 1:40 | 0.02:0.8 |
| Compound X.011 | Tricyclazole | 1:250 | 0.08:20 |
| Compound X.011 | Tricyclazole | 1:500 | 0.04:20 |
| Compound X.011 | Tricyclazole | 1:1000 | 0.02:20 |
| Compound X.011 | Tricyclazole | 1:2000 | 0.02:40 |
| Compound X.011 | Tricyclazole | 1:4000 | 0.02:80 |

Example B2: *Fusarium culmorum* (Root Rot)

Conidia of the fungus from cryogenic storage were directly mixed into nutrient broth (PDB potato dextrose broth). A DMSO solution of the test compounds was placed into a microtiter plate (96-well format) and the nutrient broth containing the fungal spores was added to it. The test plates were incubated at 24° C. and the inhibition of growth was determined photometrically after 48 hrs.

The following mixture compositions (A:B) at the reported concentration (in ppm) gave at least 80% disease control in this test.

| Component A | Component B | Ratio A:B | Conc. (ppm) (A:B) |
|---|---|---|---|
| Compound X.011 | pydiflumetofen | 1:2.5 | 0.08:0.2 |
| Compound X.011 | pydiflumetofen | 1:5 | 0.04:0.2 |
| Compound X.011 | pydiflumetofen | 1:10 | 0.02:0.2 |
| Compound X.011 | pydiflumetofen | 1:20 | 0.02:0.4 |
| Compound X.011 | pydiflumetofen | 1:40 | 0.02:0.8 |
| Compound X.011 | azoxystrobin | 1:2.5 | 0.08:0.2 |
| Compound X.011 | azoxystrobin | 1:5 | 0.04:0.2 |
| Compound X.011 | azoxystrobin | 1:10 | 0.02:0.2 |
| Compound X.011 | azoxystrobin | 1:20 | 0.02:0.4 |
| Compound X.011 | azoxystrobin | 1:40 | 0.02:0.8 |
| Compound X.011 | chlorothalonil | 1:25 | 0.08:2 |
| Compound X.011 | chlorothalonil | 1:50 | 0.04:2 |
| Compound X.011 | chlorothalonil | 1:100 | 0.02:2 |
| Compound X.011 | chlorothalonil | 1:200 | 0.02:4 |
| Compound X.011 | chlorothalonil | 1:400 | 0.02:8 |
| Compound X.011 | cyprodinil | 1:2.5 | 0.08:0.2 |
| Compound X.011 | cyprodinil | 1:5 | 0.04:0.2 |
| Compound X.011 | cyprodinil | 1:10 | 0.02:0.2 |
| Compound X.011 | cyprodinil | 1:20 | 0.02:0.4 |
| Compound X.011 | cyprodinil | 1:40 | 0.02:0.8 |
| Compound X.011 | difenoconazole | 1:25 | 0.08:2 |
| Compound X.011 | difenoconazole | 1:50 | 0.04:2 |
| Compound X.011 | difenoconazole | 1:100 | 0.02:2 |
| Compound X.011 | difenoconazole | 1:200 | 0.02:4 |
| Compound X.011 | difenoconazole | 1:400 | 0.02:8 |
| Compound X.011 | fluazinam | 1:2.5 | 0.08:0.2 |
| Compound X.011 | fluazinam | 1:5 | 0.04:0.2 |

| Component A | Component B | Ratio A:B | Conc. (ppm) (A:B) |
|---|---|---|---|
| Compound X.011 | fluazinam | 1:10 | 0.02:0.2 |
| Compound X.011 | fluazinam | 1:20 | 0.02:0.4 |
| Compound X.011 | fluazinam | 1:40 | 0.02:0.8 |
| Compound X.011 | fludioxonil | 1:2.5 | 0.08:0.2 |
| Compound X.011 | fludioxonil | 1:5 | 0.04:0.2 |
| Compound X.011 | fludioxonil | 1:10 | 0.02:0.2 |
| Compound X.011 | fludioxonil | 1:20 | 0.02:0.4 |
| Compound X.011 | fludioxonil | 1:40 | 0.02:0.8 |
| Compound X.011 | isopyrazam | 1:25 | 0.08:2 |
| Compound X.011 | isopyrazam | 1:50 | 0.04:2 |
| Compound X.011 | isopyrazam | 1:100 | 0.02:2 |
| Compound X.011 | isopyrazam | 1:200 | 0.02:4 |
| Compound X.011 | isopyrazam | 1:400 | 0.02:8 |
| Compound X.011 | benzovindiflupyr | 1:2.5 | 0.08:0.2 |
| Compound X.011 | benzovindiflupyr | 1:5 | 0.04:0.2 |
| Compound X.011 | benzovindiflupyr | 1:10 | 0.02:0.2 |
| Compound X.011 | benzovindiflupyr | 1:20 | 0.02:0.4 |
| Compound X.011 | benzovindiflupyr | 1:40 | 0.02:0.8 |
| Compound X.011 | Pyroquilon | 1:250 | 0.08:20 |
| Compound X.011 | Pyroquilon | 1:500 | 0.04:20 |
| Compound X.011 | Pyroquilon | 1:1000 | 0.02:20 |
| Compound X.011 | Pyroquilon | 1:2000 | 0.02:40 |
| Compound X.011 | Pyroquilon | 1:4000 | 0.02:80 |
| Compound X.011 | Tricyclazole | 1:250 | 0.08:20 |
| Compound X.011 | Tricyclazole | 1:500 | 0.04:20 |
| Compound X.011 | Tricyclazole | 1:1000 | 0.02:20 |
| Compound X.011 | Tricyclazole | 1:2000 | 0.02:40 |
| Compound X.011 | Tricyclazole | 1:4000 | 0.02:80 |

Example B3: *Pyricularia oryzae* (Rice Blast)

Conidia of the fungus from cryogenic storage were directly mixed into nutrient broth (PDB potato dextrose broth). A DMSO solution of the test compounds was placed into a microtiter plate (96-well format) and the nutrient broth containing the fungal spores was added to it. The test plates were incubated at 24° C. and the inhibition of growth was determined photometrically after 72 hrs.

The following mixture compositions (A:B) at the reported concentration (in ppm) gave at least 80% disease control in this test.

| Component A | Component B | Ratio A:B | Conc. (ppm) (A:B) |
|---|---|---|---|
| Compound X.011 | pydiflumetofen | 1:2.5 | 0.08:0.2 |
| Compound X.011 | pydiflumetofen | 1:5 | 0.04:0.2 |
| Compound X.011 | pydiflumetofen | 1:10 | 0.02:0.2 |
| Compound X.011 | pydiflumetofen | 1:20 | 0.02:0.4 |
| Compound X.011 | pydiflumetofen | 1:40 | 0.02:0.8 |
| Compound X.011 | azoxystrobin | 1:2.5 | 0.08:0.2 |
| Compound X.011 | azoxystrobin | 1:5 | 0.04:0.2 |
| Compound X.011 | azoxystrobin | 1:10 | 0.02:0.2 |
| Compound X.011 | azoxystrobin | 1:20 | 0.02:0.4 |
| Compound X.011 | azoxystrobin | 1:40 | 0.02:0.8 |
| Compound X.011 | chlorothalonil | 1:25 | 0.08:2 |
| Compound X.011 | chlorothalonil | 1:50 | 0.04:2 |
| Compound X.011 | chlorothalonil | 1:100 | 0.02:2 |
| Compound X.011 | chlorothalonil | 1:200 | 0.02:4 |
| Compound X.011 | chlorothalonil | 1:400 | 0.02:8 |
| Compound X.011 | cyprodinil | 1:2.5 | 0.08:0.2 |
| Compound X.011 | cyprodinil | 1:5 | 0.04:0.2 |
| Compound X.011 | cyprodinil | 1:10 | 0.02:0.2 |
| Compound X.011 | cyprodinil | 1:20 | 0.02:0.4 |
| Compound X.011 | cyprodinil | 1:40 | 0.02:0.8 |
| Compound X.011 | difenoconazole | 1:25 | 0.08:2 |
| Compound X.011 | difenoconazole | 1:50 | 0.04:2 |
| Compound X.011 | difenoconazole | 1:100 | 0.02:2 |
| Compound X.011 | difenoconazole | 1:200 | 0.02:4 |
| Compound X.011 | difenoconazole | 1:400 | 0.02:8 |
| Compound X.011 | fluazinam | 1:2.5 | 0.08:0.2 |
| Compound X.011 | fluazinam | 1:5 | 0.04:0.2 |
| Compound X.011 | fluazinam | 1:10 | 0.02:0.2 |
| Compound X.011 | fluazinam | 1:20 | 0.02:0.4 |
| Compound X.011 | fluazinam | 1:40 | 0.02:0.8 |
| Compound X.011 | fludioxonil | 1:2.5 | 0.08:0.2 |
| Compound X.011 | fludioxonil | 1:5 | 0.04:0.2 |
| Compound X.011 | fludioxonil | 1:10 | 0.02:0.2 |
| Compound X.011 | fludioxonil | 1:20 | 0.02:0.4 |
| Compound X.011 | fludioxonil | 1:40 | 0.02:0.8 |
| Compound X.011 | isopyrazam | 1:25 | 0.08:2 |
| Compound X.011 | isopyrazam | 1:50 | 0.04:2 |
| Compound X.011 | isopyrazam | 1:100 | 0.02:2 |
| Compound X.011 | isopyrazam | 1:200 | 0.02:4 |
| Compound X.011 | isopyrazam | 1:400 | 0.02:8 |
| Compound X.011 | benzovindiflupyr | 1:2.5 | 0.08:0.2 |
| Compound X.011 | benzovindiflupyr | 1:5 | 0.04:0.2 |
| Compound X.011 | benzovindiflupyr | 1:10 | 0.02:0.2 |
| Compound X.011 | benzovindiflupyr | 1:20 | 0.02:0.4 |
| Compound X.011 | benzovindiflupyr | 1:40 | 0.02:0.8 |
| Compound X.011 | Pyroquilon | 1:250 | 0.08:20 |
| Compound X.011 | Pyroquilon | 1:500 | 0.04:20 |
| Compound X.011 | Pyroquilon | 1:1000 | 0.02:20 |
| Compound X.011 | Pyroquilon | 1:2000 | 0.02:40 |
| Compound X.011 | Pyroquilon | 1:4000 | 0.02:80 |
| Compound X.011 | Tricyclazole | 1:250 | 0.08:20 |
| Compound X.011 | Tricyclazole | 1:500 | 0.04:20 |
| Compound X.011 | Tricyclazole | 1:1000 | 0.02:20 |
| Compound X.011 | Tricyclazole | 1:2000 | 0.02:40 |
| Compound X.011 | Tricyclazole | 1:4000 | 0.02:80 |

Example B4: *Septoria tritici* (Leaf Blotch)

Conidia of the fungus from cryogenic storage were directly mixed into nutrient broth (PDB potato dextrose broth). A DMSO solution of the test compounds was placed into a microtiter plate (96-well format) and the nutrient broth containing the fungal spores was added to it. The test plates were incubated at 24° C. and the inhibition of growth was determined photometrically after 72 hrs.

The following mixture compositions (A:B) at the reported concentration (in ppm) gave at least 80% disease control in this test.

| Component A | Component B | Ratio A:B | Conc. (ppm) (A:B) |
|---|---|---|---|
| Compound X.011 | pydiflumetofen | 1:2.5 | 0.08:0.2 |
| Compound X.011 | pydiflumetofen | 1:5 | 0.04:0.2 |
| Compound X.011 | pydiflumetofen | 1:10 | 0.02:0.2 |
| Compound X.011 | pydiflumetofen | 1:20 | 0.02:0.4 |
| Compound X.011 | pydiflumetofen | 1:40 | 0.02:0.8 |
| Compound X.011 | azoxystrobin | 1:2.5 | 0.08:0.2 |
| Compound X.011 | azoxystrobin | 1:5 | 0.04:0.2 |
| Compound X.011 | azoxystrobin | 1:10 | 0.02:0.2 |
| Compound X.011 | azoxystrobin | 1:20 | 0.02:0.4 |
| Compound X.011 | azoxystrobin | 1:40 | 0.02:0.8 |
| Compound X.011 | chlorothalonil | 1:25 | 0.08:2 |
| Compound X.011 | chlorothalonil | 1:50 | 0.04:2 |
| Compound X.011 | chlorothalonil | 1:100 | 0.02:2 |
| Compound X.011 | chlorothalonil | 1:200 | 0.02:4 |
| Compound X.011 | chlorothalonil | 1:400 | 0.02:8 |
| Compound X.011 | difenoconazole | 1:25 | 0.08:2 |
| Compound X.011 | difenoconazole | 1:50 | 0.04:2 |
| Compound X.011 | difenoconazole | 1:100 | 0.02:2 |
| Compound X.011 | difenoconazole | 1:200 | 0.02:4 |
| Compound X.011 | difenoconazole | 1:400 | 0.02:8 |
| Compound X.011 | fluazinam | 1:2.5 | 0.08:0.2 |
| Compound X.011 | fluazinam | 1:5 | 0.04:0.2 |
| Compound X.011 | fluazinam | 1:10 | 0.02:0.2 |

| Component A | Component B | Ratio A:B | Conc. (ppm) (A:B) |
|---|---|---|---|
| Compound X.011 | fluazinam | 1:20 | 0.02:0.4 |
| Compound X.011 | fluazinam | 1:40 | 0.02:0.8 |
| Compound X.011 | fludioxonil | 1:20 | 0.02:0.4 |
| Compound X.011 | fludioxonil | 1:40 | 0.02:0.8 |
| Compound X.011 | isopyrazam | 1:25 | 0.08:2 |
| Compound X.011 | isopyrazam | 1:50 | 0.04:2 |
| Compound X.011 | isopyrazam | 1:100 | 0.02:2 |
| Compound X.011 | isopyrazam | 1:200 | 0.02:4 |
| Compound X.011 | isopyrazam | 1:400 | 0.02:8 |
| Compound X.011 | benzovindiflupyr | 1:2.5 | 0.08:0.2 |
| Compound X.011 | benzovindiflupyr | 1:5 | 0.04:0.2 |
| Compound X.011 | benzovindiflupyr | 1:10 | 0.02:0.2 |
| Compound X.011 | benzovindiflupyr | 1:20 | 0.02:0.4 |
| Compound X.011 | benzovindiflupyr | 1:40 | 0.02:0.8 |

Example B5: *Venturia inequalis* (Apple Scab)

Conidia of the fungus from cryogenic storage were directly mixed into nutrient broth (PDB potato dextrose broth). A DMSO solution of the test compounds was placed into a microtiter plate (96-well format) and the nutrient broth containing the fungal spores was added to it. The test plates were incubated at 24° C. and the inhibition of growth was determined photometrically after 7 days at 620 nm.

The following mixture compositions (A:B) at the reported concentration (in ppm) gave at least 80% disease control in this test.

| Component A | Component B | Ratio A:B | Conc. (ppm) (A:B) |
|---|---|---|---|
| Compound X.011 | pydiflumetofen | 1:2.5 | 0.08:0.2 |
| Compound X.011 | pydiflumetofen | 1:5 | 0.04:0.2 |
| Compound X.011 | pydiflumetofen | 1:10 | 0.02:0.2 |
| Compound X.011 | pydiflumetofen | 1:20 | 0.02:0.4 |
| Compound X.011 | pydiflumetofen | 1:40 | 0.02:0.8 |
| Compound X.011 | azoxystrobin | 1:2.5 | 0.08:0.2 |
| Compound X.011 | azoxystrobin | 1:5 | 0.04:0.2 |
| Compound X.011 | azoxystrobin | 1:10 | 0.02:0.2 |
| Compound X.011 | azoxystrobin | 1:20 | 0.02:0.4 |
| Compound X.011 | azoxystrobin | 1:40 | 0.02:0.8 |
| Compound X.011 | chlorothalonil | 1:25 | 0.08:2 |
| Compound X.011 | chlorothalonil | 1:50 | 0.04:2 |
| Compound X.011 | chlorothalonil | 1:100 | 0.02:2 |
| Compound X.011 | chlorothalonil | 1:200 | 0.02:4 |
| Compound X.011 | chlorothalonil | 1:400 | 0.02:8 |
| Compound X.011 | cyprodinil | 1:2.5 | 0.08:0.2 |
| Compound X.011 | cyprodinil | 1:5 | 0.04:0.2 |
| Compound X.011 | cyprodinil | 1:10 | 0.02:0.2 |
| Compound X.011 | cyprodinil | 1:20 | 0.02:0.4 |
| Compound X.011 | cyprodinil | 1:40 | 0.02:0.8 |
| Compound X.011 | difenoconazole | 1:25 | 0.08:2 |
| Compound X.011 | difenoconazole | 1:50 | 0.04:2 |
| Compound X.011 | difenoconazole | 1:100 | 0.02:2 |
| Compound X.011 | difenoconazole | 1:200 | 0.02:4 |
| Compound X.011 | difenoconazole | 1:400 | 0.02:8 |
| Compound X.011 | fluazinam | 1:2.5 | 0.08:0.2 |
| Compound X.011 | fluazinam | 1:5 | 0.04:0.2 |
| Compound X.011 | fluazinam | 1:10 | 0.02:0.2 |
| Compound X.011 | fluazinam | 1:20 | 0.02:0.4 |
| Compound X.011 | fluazinam | 1:40 | 0.02:0.8 |
| Compound X.011 | fludioxonil | 1:2.5 | 0.08:0.2 |
| Compound X.011 | fludioxonil | 1:10 | 0.02:0.2 |
| Compound X.011 | fludioxonil | 1:20 | 0.02:0.4 |
| Compound X.011 | fludioxonil | 1:40 | 0.02:0.8 |
| Compound X.011 | isopyrazam | 1:25 | 0.08:2 |
| Compound X.011 | isopyrazam | 1:50 | 0.04:2 |
| Compound X.011 | isopyrazam | 1:100 | 0.02:2 |
| Compound X.011 | isopyrazam | 1:200 | 0.02:4 |
| Compound X.011 | isopyrazam | 1:400 | 0.02:8 |
| Compound X.011 | benzovindiflupyr | 1:2.5 | 0.08:0.2 |
| Compound X.011 | benzovindiflupyr | 1:5 | 0.04:0.2 |
| Compound X.011 | benzovindiflupyr | 1:10 | 0.02:0.2 |
| Compound X.011 | benzovindiflupyr | 1:20 | 0.02:0.4 |
| Compound X.011 | benzovindiflupyr | 1:40 | 0.02:0.8 |
| Compound X.011 | Pyroquilon | 1:2000 | 0.02:40 |
| Compound X.011 | Pyroquilon | 1:4000 | 0.02:80 |
| Compound X.011 | Tricyclazole | 1:250 | 0.08:20 |
| Compound X.011 | Tricyclazole | 1:1000 | 0.02:20 |
| Compound X.011 | Tricyclazole | 1:2000 | 0.02:40 |
| Compound X.011 | Tricyclazole | 1:4000 | 0.02:80 |

What is claimed is:

1. A fungicidal composition comprising a mixture of components (A) and (B), wherein component (A) is a compound of formula (I)

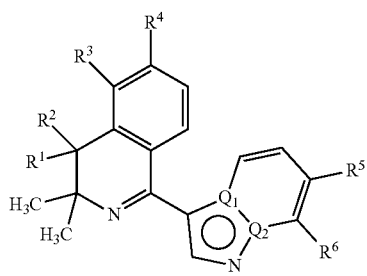

wherein
$Q_1$ is a nitrogen atom and $Q_2$ is a carbon atom; or
$Q_1$ is a carbon atom and $Q_2$ is a nitrogen atom; and
$R^1$ is fluoro or methyl;
$R^2$ is fluoro or methyl;
$R^3$ is hydrogen or fluoro;
$R^4$ is hydrogen, or fluoro;
$R^5$ is hydrogen, methyl, ethyl, fluoro, chloro or bromo;
$R^6$ is hydrogen or methyl; or a salt, enantiomer, tautomer, or N-oxide thereof; and
component (B) is a compound selected from the group consisting of:
Pydiflumetofen,
Benzovindiflupyr,
Difenoconazole,
Hexaconazole,
Azoxystrobin,
Fludioxonil,
Cyprodinil,
Fluazinam,
Isopyrazam,
Pyroquilon,
Tricyclazole,
Chlorothalonil,
Propiconazole,
Penconazole,
Fenpropimorph,
Fenpropidin,
Sulfur, and
*Bacillus subtilis* var. *amyloliquefaciens* Strain FZB24,
wherein the weight ratio of component (A) to component (B) is from 20:1 to 1:40.

2. The fungicidal composition according claim 1, wherein component (A) is a compound selected from:

1-(6-chloro-7-methyl-pyrazolo[1,5-a]pyridin-3-yl)-4,4-difluoro-3,3-dimethyl-isoquinoline,
4,4-difluoro-1-(6-fluoro-7-methyl-pyrazolo[1,5-a]pyridin-3-yl)-3,3-dimethyl-isoquinoline,
4,4-difluoro-3,3-dimethyl-1-(6-methylpyrazolo[1,5-a]pyridin-3-yl)isoquinoline,
1-(6,7-dimethylpyrazolo[1,5-a]pyridin-3-yl)-4,4,5-trifluoro-3,3-dimethyl-isoquinoline,
1-(6,7-dimethylpyrazolo[1,5-a]pyridin-3-yl)-4,4-difluoro-3,3-dimethyl-isoquinoline, and
1-(7,8-dimethylimidazo[1,2-a]pyridin-3-yl)-4,4-difluoro-3,3-dimethyl-isoquinoline; or
a salt, enantiomer, tautomer or N-oxide of one of those compounds.

3. The fungicidal composition according to claim 1, wherein component (A) is 1-(6-chloro-7-methyl-pyrazolo[1,5-a]pyridin-3-yl)-4,4-difluoro-3,3-dimethyl-isoquinoline; or a salt, enantiomer, tautomer or N-oxide thereof.

4. The fungicidal composition according to claim 1, wherein component (A) is 4,4-difluoro-1-(6-fluoro-7-methyl-pyrazolo[1,5-a]pyridin-3-yl)-3,3-dimethyl-isoquinoline; or a salt, enantiomer, tautomer or N-oxide thereof.

5. The fungicidal composition according to claim 1, wherein component (A) is 4,4-difluoro-3,3-dimethyl-1-(6-methylpyrazolo[1,5-a]pyridin-3-yl)isoquinoline; or a salt, enantiomer, tautomer or N-oxide thereof.

6. The fungicidal composition according to claim 1, wherein component (A) is 1-(6,7-dimethylpyrazolo[1,5-a]pyridin-3-yl)-4,4-difluoro-3,3-dimethyl-isoquinoline; or a salt, enantiomer, tautomer or N-oxide thereof.

7. The fungicidal composition according to claim 1, wherein component (A) is 1-(7,8-dimethylimidazo[1,2-a]pyridin-3-yl)-4,4-difluoro-3,3-dimethyl-isoquinoline; or a salt, enantiomer, tautomer or N-oxide thereof.

8. The fungicidal composition according to claim 1, wherein component (B) is a compound selected from the group consisting of Pydiflumetofen, Benzovindiflupyr, Difenoconazole, Azoxystrobin, Fludioxonil, Fluazinam, Cyprodinil, Isopyrazam, Pyroquilon, Tricyclazole and Chlorothalonil.

9. The fungicidal composition according to claim 1, wherein component (B) is a compound selected from the group consisting of Pydiflumetofen, Difenoconazole, Azoxystrobin, Fludioxonil, Cyprodinil and Pyroquilon.

10. The fungicidal composition according to claim 1, further comprising of the following:
a fungicide, selected from etridiazole, benalaxyl, benalaxyl-M, furalaxyl, metalaxyl, metalaxyl-M, dodicin, N'-(2,5-Dimethyl-4-phenoxy-phenyl)-N-ethyl-N-methyl-formamidine, N'-[4-(4,5-Dichloro-thiazol-2-yloxy)-2,5-dimethyl-phenyl]-N-ethyl-N-methyl-formamidine, N'-[4-[[3-[(4-chlorophenyl)methyl]-1,2,4-thiadiazol-5-yl]oxy]-2,5-dimethyl-phenyl]-N-ethyl-N-methyl-formamidine, ethirimol, 3'-chloro-2-methoxy-N-[(3RS)-tetrahydro-2-oxofuran-3-yl]acet-2',6'-xylidide, mepanipyrim, pyrimethanil, dithianon, aureofungin, blasticidin-S, biphenyl, chloroneb, dicloran, hexachlorobenzene, quintozene, tecnazene, tolclofos-methyl, metrafenone, 2,6-dichloro-N-(4-trifluoromethylbenzyl)-benzamide, fluopicolide, tioxymid, flusulfamide, benomyl, carbendazim, carbendazim chlorhydrate, chlorfenazole, fuberidazole, thiabendazole, thiophanate-methyl, benthiavalicarb, chlobenthiazone, probenazole, acibenzolar, bethoxazin, pyrifenone, acibenzolar-S-methyl, pyribencarb, butylamine, 3-iodo-2-propinyl n-butylcarbamate, iodocarb (isopropanyl butylcarbamate), isopropanyl butylcarbamate, picarbutrazox, polycarbamate, propamocarb, tolprocarb, 3-(difluoromethyl)-N-(7-fluoro-1,1,3,3-tetramethyl-indan-4-yl)-1-methyl-pyrazole-4-carboxamide diclocymet, N-[(5-chloro-2-isopropyl-phenyl)methyl]-N-cyclopropyl-3-(difluoromethyl)-5-fluoro-1-methyl-pyrazole-4-carboxamide N-cyclopropyl-3-(difluoromethyl)-5-fluoro-N-[(2-isopropylphenyl)methyl]-1-methyl-pyrazole-4-carboxamide carpropamid, flumorph, oxine-copper, cymoxanil, phenamacril, cyazofamid, flutianil, thicyofen, chlozolinate, iprodione, procymidone, vinclozolin, bupirimate, dinocton, dinopenton, dinobuton, dinocap, meptyldinocap, diphenylamine, phosdiphen, 2,6-dimethyl-[1,4]dithiino[2,3-c:5,6-c']dipyrrole-1,3,5,7(2H,6H)-tetraone, azithiram, etem, ferbam, mancozeb, maneb, metam, metiram, metiram-zinc, nabam, propineb, thiram, vapam, zineb, ziram, dithioether, isoprothiolane, ethaboxam, fosetyl, phosetyl-Al, methyl bromide, methyl iodide, methyl isothiocyanate, cyclafuramid, fenfuram, validamycin, streptomycin, (2RS)-2-bromo-2-(bromomethyl)glutaronitrile, dodine, doguadine, guazatine, iminoctadine, iminoctadine triacetate, 2,4-D, 2,4-DB, kasugamycin, dimethirimol, fenhexamid, hymexazole, hydroxyisoxazole imazalil, imazalil sulphate, oxpoconazole, pefurazoate, prochloraz, triflumizole, fenamidone, Bordeaux mixture, calcium polysulfide, copper acetate, copper carbonate, copper hydroxide, copper naphthenate, copper oleate, copper oxychloride, copper oxyquinolate, copper silicate, copper sulphate, copper tallate, cuprous oxide, sulphur, carbaryl, phthalide, dingjunezuo, oxathiapiprolin, fluoroimide, mandipropamid, KSF-1002, benzamorf, dimethomorph, tridemorph, dodemorph, diethofencarb, fentin acetate, fentin hydroxide, carboxin, oxycarboxin, drazoxolon, famoxadone, m-phenylphenol, p-phenylphenol, tribromophenol, 2-[2-[(7,8-difluoro-2-methyl-3-quinolyl)oxy]-6-fluoro-phenyl]propan-2-ol 2-[2-fluoro-6-[(8-fluoro-2-methyl-3-quinolyl)oxy]phenyl]propan-2-ol cyflufenamid, ofurace, oxadixyl, flutolanil, mepronil, isofetamid, fenpiclonil, pencycuron, edifenphos, iprobenfos, pyrazophos, phosphorus acids, tecloftalam, captafol, captan, ditalimfos, triforine, fenpropidin, piperalin, osthol, 1-methylcyclopropene, 4-CPA, chlormequat, clofencet, dichlorprop, dimethipin, endothal, ethephon, flumetralin, forchlorfenuron, gibberellic acid, gibberellins, hymexazol, maleic hydrazide, mepiquat, naphthalene acetamide, paclobutrazol, prohexadione, prohexadione-calcium, thidiazuron, tributyl phosphorotrithioate, trinexapac, uniconazole, α-naphthalene acetic acid, polyoxin D, BLAD, chitosan, fenoxanil, folpet, 3-(difluoromethyl)-N-methoxy-1-methyl-N-[1-methyl-2-(2,4,6-trichlorophenyl)ethyl]pyrazole-4-carboxamide, bixafen, fluxapyroxad, furametpyr, penflufen, penthiopyrad, sedaxane, fenpyrazamine, diclomezine, pyrifenox, boscalid, fluopyram, diflumetorim, fenarimol, 5-fluoro-2-(p-tolylmethoxy)pyrimidin-4-amine ferimzone, dimetachlone, proquinazid, ethoxyquin, quinoxyfen, 4,4,5-trifluoro-3,3-dimethyl-1-(3-quinolyl)isoquinoline 4,4-difluoro-3,3-dimethyl-1-(3-quinolyl)isoquinoline 5-fluoro-3,3,4,4-tetramethyl-1-(3-quinolyl)isoquinoline 9-fluoro-2,2-dimethyl-5-(3-quinolyl)-3H-1,4-benzoxazepine, tebufloquin, oxolinic acid, chinomethionate, spiroxamine, (E)-N-methyl-2-[2-(2,5-dimethylphenoxymethyl)phenyl]-2-methoxy-imino-acetamide, coumoxystrobin, dimoxystrobin, enestroburin, enoxastrobin fenamistrobin, flufenoxystrobin, fluoxastrobin, kresoxim-methyl, mandestrobin, metaminostrobin, metominostrobin, orysastrobin, picoxystrobin, pyraclostrobin, pyrametostrobin, pyraoxystrobin, triclopyricarb, trifloxystrobin, amisulbrom, dichlofluanid, tolylfluanid, but-3-ynyl N-[6-[[(Z)-[(1-methyltetrazol-5-yl)-phenyl-methylene]amino]oxymethyl]-2-pyridyl]carbamate, dazomet, isotianil, tiadinil, thifluzamide, benthiazole, silthiofam, zoxamide, anilazine, (+−)-cis-1-(4-chlorophenyl)-2-(1H-1,2,4-triazol-1-yl)-cycloheptanol (huanjunzuo), 145-bromo-2-pyridyl)-2-(2,4-difluorophenyl)-1,1-difluoro-3-(1,2,4-triazol-1-yl)propan-2-ol 2-(1-tert-butyl)-1-(2-chlorophenyl)-3-(1,2,4-triazol-1-yl)-propan-2-ol, azaconazole, bitertanol, bromuconazole, climbazole, cyproconazole, dimetconazole, diniconazole, diniconazole-M, epoxiconazole, etaconazole, fenbuconazole, fluquinconazole, flusilazole, flutriafol, imibenconazole, ipconazole, metconazole, myclobutanil, prothioconazole, Mefentrifluconazole, simeconazole, tebuconazole, tetraconazole, triadimefon, triadimenol, triazoxide, triticonazole, 2-[[(1R,5S)-5-[(4-fluorophenyl)methyl]-1-hydroxy-2,2-dimethyl-cyclopentyl]methyl]-4H-1,2,4-triazole-3-thione 2-[[3-(2-chlorophenyl)-2-(2,4-difluorophenyl)oxiran-2-yl]methyl]-4H-1,2,4-triazole-3-thione, ametoctradin, iprovalicarb, valifenalate, 2-benzyl-4-chlorophenol, allyl alcohol, azafenidin, benzalkonium chloride, chloropicrin, cresol, daracide, dichlorophen, difenzoquat, dipyrithione, N-(2-p-chlorobenzoylethyl)-hexaminium chloride, NNF-0721, octhilinone, oxasulfuron, ipflufenoquin, quinofumelin, dipymetitrone, fenpicoxamid, 3-chloro-4-(2,6-difluorophenyl)-6-methyl-5-phenyl-pyridazine, isoflucypram, fluindapyr, isofetamid, pyraziflumid, inpyrfluxam, N-[2-[2,4-dichloro-phenoxy]phenyl]-3-(difluoromethyl)-1-methyl-pyrazole-4-carboxamide, N-[2-[2-chloro-4-(trifluoromethyl)phenoxy]phenyl]-3-(difluoromethyl)-1-methyl-pyrazole-4-carboxamide, mandestrobin, metyltetraprole, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate, dichlobentiazox, phenamacril, aminopyrifen, fluopimomide, florylpicoxamid, pyrapropoyne, pycarbutrazox, 4-[[6-[2-(2,4-difluorophenyl)-1,1-difluoro-2-hydroxy-3-(1,2,4-triazol-1-yl)propyl]-3-pyridyl]oxy] benzonitrile, propamidine and propionic acid; or an insecticide selected from abamectin, acephate, acetamiprid, amidoflumet, avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim, flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; or a bactericide selected from streptomycin; or an acaricide selected from amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; or a biological agent selected from *Bacillus thuringiensis*, *Bacillus thuringiensis* delta endotoxin, baculovirus, and entomopathogenic bacteria, virus and fungi.

11. The fungicidal composition according to claim 1, wherein the composition further comprises an agriculturally acceptable carrier and, optionally, a surfactant and/or formulation adjuvants.

12. The fungicidal composition according to claim 1, wherein the weight ratio of component (A) to component (B) is from 15:1 to 1:30.

13. The fungicidal composition according to claim 1, wherein the weight ratio of component (A) to component (B) is from 10:1 to 1:20.

14. A method of controlling phytopathogenic fungi on useful plants or on propagation material thereof, comprising: applying to the useful plants, the locus thereof or propagation material thereof a fungicidal composition as defined in claim 1.

15. The method according to claim 14, wherein the composition components (A) and (B) are applied in a sequential manner.

16. The fungicidal composition according to claim 1, wherein component (A) is a compound selected from:
1-(6-chloro-7-methyl-pyrazolo[1,5-a]pyridin-3-yl)-4,4-difluoro-3,3-dimethyl-isoquinoline, 4,4-difluoro-1-(6-fluoro-7-methyl-pyrazolo[1,5-a]pyridin-3-yl)-3,3-dimethyl-isoquinoline, 4,4-difluoro-3,3-dimethyl-1-(6-methylpyrazolo[1,5-a]pyridin-3-yl)isoquinoline, 1-(6,7-dimethylpyrazolo[1,5-a]pyridin-3-yl)-4,4,5-trifluoro-3,3-dimethyl-isoquinoline, 1-(6,7-dimethylpyrazolo[1,5-a]pyridin-3-yl)-4,4-difluoro-3,3-dimethyl-isoquinoline, and 1-(7,8-dimethylimidazo[1,2-a]pyridin-3-yl)-4,4-difluoro-3,3-dimethyl-isoquinoline.

17. The fungicidal composition according claim 8, wherein component (A) is a compound selected from:
1-(6-chloro-7-methyl-pyrazolo[1,5-a]pyridin-3-yl)-4,4-difluoro-3,3-dimethyl-isoquinoline, 4,4-difluoro-1-(6-fluoro-7-methyl-pyrazolo[1,5-a]pyridin-3-yl)-3,3-dimethyl-isoquinoline, 4,4-difluoro-3,3-dimethyl-1-(6-methylpyrazolo[1,5-a]pyridin-3-yl)isoquinoline, 1-(6,7-dimethylpyrazolo[1,5-a]pyridin-3-yl)-4,4,5-trifluoro-3,3-dimethyl-isoquinoline, 1-(6,7-dimethylpyrazolo[1,5-a]pyridin-3-yl)-4,4-difluoro-3,3-dimethyl-isoquinoline, and 1-(7,8-dimethylimidazo[1,2-a]pyridin-3-yl)-4,4-difluoro-3,3-dimethyl-isoquinoline.

18. A composition comprising:
1-(6,7-dimethylpyrazolo[1,5-a]pyridin-3-yl)-4,4-difluoro-3,3-dimethyl-isoquinoline; and a component selected from Pydiflumetofen, Azoxystrobin, Chlorothalonil, Cyprodinil, Difenoconazole, Fluazinam, Isopyrazam, Benzovindiflupyr, Pyroquilon, or Tricyclazole;
wherein the weight ratio of 1-(6,7-dimethylpyrazolo[1,5-a]pyridin-3-yl)-4,4-difluoro-3,3-dimethyl-isoquinoli to the component is from 20:1 to 1:40.

19. The composition of claim 18, wherein the weight ratio of 1-(6,7-dimethylpyrazolo[1,5-a]pyridin-3-yl)-4,4-difluoro-3,3-dimethyl-isoquinoli to the component is 10:1 to 1:20.

20. The composition of claim 18, wherein the weight ratio of 1-(6,7-dimethylpyrazolo[1,5-a]pyridin-3-yl)-4,4-difluoro-3,3-dimethyl-isoquinoli to the component is 5:1 to 1:10.

* * * * *